(12) United States Patent
Terada et al.

(10) Patent No.: US 9,117,124 B2
(45) Date of Patent: *Aug. 25, 2015

(54) DRIVING ATTENTION AMOUNT DETERMINATION DEVICE, METHOD, AND COMPUTER PROGRAM

(71) Applicant: Panasonic Corporation, Osaka (JP)

(72) Inventors: Yoshihisa Terada, Osaka (JP); Koji Morikawa, Kyoto (JP)

(73) Assignee: Panasonic Intellectual Property Management Co., Ltd, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/247,550

(22) Filed: Apr. 8, 2014

(65) Prior Publication Data
US 2014/0226013 A1    Aug. 14, 2014

Related U.S. Application Data

(60) Division of application No. 13/192,818, filed on Jul. 28, 2011, now Pat. No. 8,730,326, which is a continuation of application No. PCT/JP2010/006112, filed on Oct. 14, 2010.

(51) Int. Cl.
*H04N 7/18* (2006.01)
*G06K 9/00* (2006.01)
(Continued)

(52) U.S. Cl.
CPC .......... *G06K 9/00845* (2013.01); *A61B 5/0006* (2013.01); *A61B 5/04004* (2013.01);
(Continued)

(58) Field of Classification Search
CPC ........ B60R 1/00; H01N 7/181; G01B 11/022; A61B 1/041

USPC .................................... 348/148, 143, 135, 77
See application file for complete search history.

(56) References Cited

U.S. PATENT DOCUMENTS 5,311,877 A    5/1994  Kishi
5,813,993 A *  9/1998  Kaplan et al. ................. 600/544
(Continued)

FOREIGN PATENT DOCUMENTS

EP    2312551 A1    4/2011
JP    05-092039 A    4/1993
(Continued)

OTHER PUBLICATIONS

Miura et al., "Jikoto Anzenno Shinrigaku" or "Psychology of Accidents and Safety", 2007, p. 131, University of Tokyo press (cited in [0084] of the specification), and partial translation thereof, previously cited in IDS filed Jul. 28, 2011.
(Continued)

*Primary Examiner* — Shawn An
(74) *Attorney, Agent, or Firm* — Renner, Otto, Boisselle & Sklar, LLP

(57) ABSTRACT

A driving attention amount determination apparatus includes: an electroencephalogram measurement section for measuring an electroencephalogram signal of a driver; a central stimulation presentation section for presenting a visual stimulation in a central visual field of the driver; a peripheral stimulation presentation section for presenting a visual stimulation in a peripheral visual field of the driver; a threshold setting section for setting a determination threshold for attention amount determination from a distribution of amplitude of an event-related potential in the electroencephalogram signal based on a point of presenting the stimulation in the central visual field as a starting point; and an attention amount determination section for determining an attention amount through a comparison between the determination threshold and an amplitude of an event-related potential in the electroencephalogram signal based on a point of presenting the stimulation in the peripheral visual field as a starting point.

9 Claims, 23 Drawing Sheets

(51) Int. Cl.
*B60R 1/00* (2006.01)
*G01B 11/02* (2006.01)
*A61B 5/00* (2006.01)
*A61B 5/04* (2006.01)
*A61B 5/0476* (2006.01)
*A61B 5/0484* (2006.01)
*A61B 5/18* (2006.01)
*G08B 21/02* (2006.01)
*A61B 1/04* (2006.01)

(52) U.S. Cl.
CPC ........... *A61B5/0476* (2013.01); *A61B 5/04842* (2013.01); *A61B 5/18* (2013.01); *A61B 5/4035* (2013.01); *B60R 1/00* (2013.01); *G01B 11/022* (2013.01); *G08B 21/02* (2013.01); *H04N 7/181* (2013.01); *A61B 1/041* (2013.01); *A61B 5/6814* (2013.01); *A61B 2503/22* (2013.01)

(56) References Cited

U.S. PATENT DOCUMENTS

| | | | | |
|---|---|---|---|---|
| 8,730,326 | B2* | 5/2014 | Terada et al. | 348/148 |
| 2004/0044293 | A1 | 3/2004 | Burton | |
| 2009/0112287 | A1* | 4/2009 | Greenberg et al. | 607/54 |
| 2009/0171232 | A1 | 7/2009 | Hu et al. | |
| 2010/0156617 | A1* | 6/2010 | Nakada et al. | 340/439 |

FOREIGN PATENT DOCUMENTS

| | | |
|---|---|---|
| JP | 2002-127780 A | 5/2002 |
| JP | 2004-178367 A | 6/2004 |
| JP | 2005-034620 A | 2/2005 |
| JP | 2007-202882 A | 8/2007 |
| JP | 2009-022370 A | 2/2009 |

OTHER PUBLICATIONS

Yamada et al., "Yokuwakaru Shinritoukei" or "Psychological Statistics Made Easy", 2004, pp. 30-33 and p. 55, Minerva Shobo (cited in [0103] and [0111] of the specification), and partial translation thereof, previously cited in IDS filed Jul. 28, 2011.

Ebe et al., "Technique for Measuring Driver's Attention Level by Using Event-Related Potentials", Automotive Technologies, vol. 58, No. 7, pp. 91-96, 2004 with English Abstract (cited in [0008] of the specification).

"Jishoukanrenden I (ERP) Manyuaru-P300 Wo Chusinni" or "Event-Related Potential (ERP) Manual-Mainly Concerning P300", edited by Kimitaka Kaga et al., Shinohara Shuppan Shinsha, (1995), p. 30, (cited in [0073] of the specification), with partial English translation.

Miyata et al., "New Physiopsychology", 1998, pp. 119-120 and 110, Kitaoji Shobo and Partial English translation (cited in [0127] of the specification).

"Jishoukanrenden I (ERP) Manyuaru-P300 Wo Chusinni" or "Event-Related Potential (ERP) Manual-Mainly Concerning P300", edited by Kinitaka et al., Shinohara Shuppan Shinsha, (1995), p. 30, University of Tokyo press (cited in [0073] of the specification).

Extended European Search Report for corresponding European Application No. 10823204.2, dated Nov. 12, 2014.

* cited by examiner

RELATIONSHIP BETWEEN MEDIAN OF CENTRAL STIMULATION-P300 DISTRIBUTION AND OPTIMUM THRESHOLD IN EACH TEST SUBJECT (10 TEST SUBJECTS)

| STIMULATION POSITION (VIEWING ANGLE: DEGREES) | (-120,0) | (100,10) | (10,5) | (-100,10) | (-120,-10) | ... |
|---|---|---|---|---|---|---|
| VISUAL REGION | PERIPHERAL | PERIPHERAL | CENTRAL | PERIPHERAL | PERIPHERAL | |
| TIMING OF PRESENTATION (TIME) | 10:21:13 | 10:21:30 | 10:21:48 | 10:22:05 | 10:22:15 | ... |
| ATTENTION AMOUNT | DISTRACTED | DISTRACTED | - | FOCUSED | FOCUSED | ... |

141

|  | AVERAGE DISTINCTION RATE | TEST SUBJECT A | TEST SUBJECT B | TEST SUBJECT C | TEST SUBJECT D |
|---|---|---|---|---|---|
| PRESENT INVENTION | 71.3 | 84.7 | 66.1 | 63.3 | 71.2 |
| OPTIMUM THRESHOLD IS USED | 73.7 | 84.9 | 75.0 | 63.3 | 71.5 |
| AVERAGE OPTIMUM THRESHOLD | 66.1 | 80.7 | 57.1 | 62.2 | 63.8 |

UNIT (%)

| TIMING OF PRESENTATION (DATE, TIME) | 8/20 10:21:13 | 8/20 10:21:30 | 8/20 10:22:05 | 8/20 10:22:15 | ... |
|---|---|---|---|---|---|
| P300 AMPLITUDE (μV) | 22.5 | 28.9 | 13.9 | 38.4 | ... |

*FIG.32A*
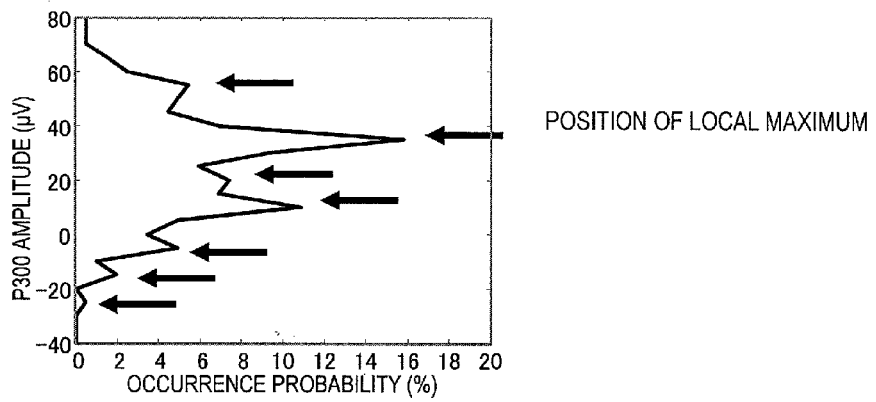
POSITION OF LOCAL MAXIMUM
*FIG.32B*
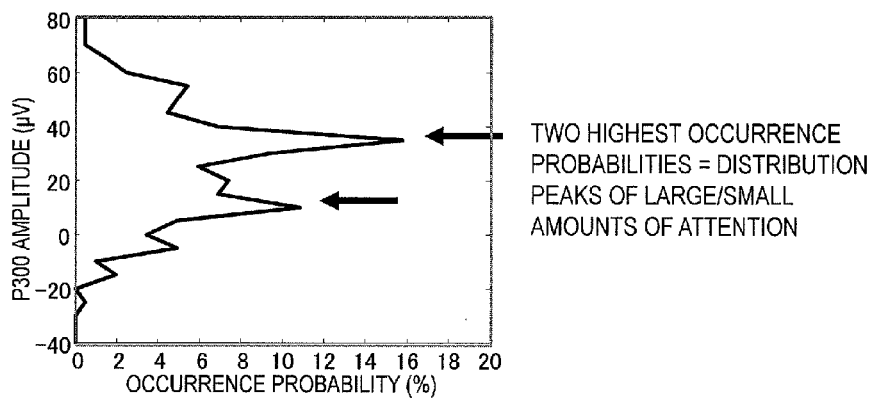
TWO HIGHEST OCCURRENCE PROBABILITIES = DISTRIBUTION PEAKS OF LARGE/SMALL AMOUNTS OF ATTENTION
*FIG.33*
| | AVERAGE DISTINCTION RATE | TEST SUBJECT A | TEST SUBJECT B | TEST SUBJECT C | TEST SUBJECT D |
|---|---|---|---|---|---|
| PRESENT INVENTION (EMBODIMENT 2) | 68.7 | 81.5 | 62.5 | 59.2 | 71.5 |
UNIT (%)

DRIVING ATTENTION AMOUNT DETERMINATION DEVICE, METHOD, AND COMPUTER PROGRAM

This application is a divisional of U.S. application Ser. No. 13/192,818 filed Jul. 28, 2011 which is a continuation of International Application No. PCT/JP2010/006112, with an international filing date of Oct. 14, 2010, which claims priority of Japanese Patent Application No. 2009-238057, filed on Oct. 15, 2009, the contents of which are hereby incorporated by reference.

BACKGROUND OF THE INVENTION

1. Field of the Invention

The present invention relates to a driving attention amount determination apparatus, method, and computer program which determines the state of attention of a driver by utilize correspond an electroencephalogram and provides safe driving assistance.

2. Description of the Related Art

In recent years, in connection with accident prevention apparatuses related to automobile driving, methods of determining the state of a driver, and providing driving assistance based on the result of determination are being studied. One visual perception function of a driver that is necessary for safe driving is detection of dangerous objects. Detection of dangerous objects involves noticing, in the peripheral visual field, any dangerous motion of vehicles and pedestrians in the surroundings. A deterioration in this function may lead to cross-collision accidents and rush-out accidents.

A "peripheral visual field" generally refers to, within the entire field of vision defined by a range spanning 130 degrees in up and down directions and 180 degrees in right and left directions, the range outside a range of about 40 degrees (central visual field) that is centered around a line of sight. As is known, in the peripheral visual field, it is difficult to recognize the shape and color of an object in detail, but sensitive response occurs with respect to any object that changes in time, e.g., a moving object or flickering light. In anticipation of a rushing out of a pedestrian or a motorcycle passing on the side, etc., a driver needs to pay attention to the peripheral visual region and any door mirrors or the like existing in this region. Therefore, when the amount of attention of the driver to the peripheral visual region becomes low, a remedy such as issuing an alarm to the driver is needed.

One method of determining the state of attention of a driver employs a camera which is aimed at the driver for detecting the line of sight and motions of the face of the driver, and determines an allocation of attention of the driver. For example, Japanese Laid-Open Patent Publication No. 2004-178367 discloses a technique of determining the attention allocation of a driver by comparing a fixation point, which is detected from the line of sight and motions of the face of the driver, against an optimum fixation position that the driver should pay attention to, which is determined from the ambient situation of the driver's vehicle.

Another method determines the state of attention of a driver based on changes in the traveling velocity and the steering angle of the steering wheel and the like, which reflect the manner in which the driver's vehicle is being operated. For example, Japanese Laid-Open Patent Publication No. 2002-127780 discloses a technique which determines a driver's degree of concentration on driving by using a brake response time with respect to a sudden deceleration of a car traveling that is ahead (hereinafter referred to as a "preceding vehicle") or the like, thus determining the level of need to output an alarm to the driver.

On the other hand, studies are under way to examine the amount of attention of a driver to driving by utilizing an event-related potential (ERP) of his or her electroencephalogram. An "event-related potential" refers to a transient potential fluctuation in the brain which occurs in temporal relationship with an external or internal event. When examining the amount of attention of a driver to driving, the so-called "P300" is utilized. "P300" refers to a positive component of an event-related potential in the electroencephalogram which appears near about 300 milliseconds based on the timing of an external visual stimulation or the like as a starting point. P300 is supposed to reflect perception of, or attention to, a stimulation.

For example, "Technique for Measuring Driver's Attention Level by Using Event-Related Potentials", Ebe et al., Automotive Technologies, Vol. 58, No. 7, pp. 91-96, 2004 (hereinafter referred to as "Non-Patent Document 1") discloses a study concerning the measurement of an amount of driving attention by utilizing an event-related potential. In this study, in an experiment of trying to drive a vehicle so as to follow a preceding vehicle, the driver is asked to perform a task of stepping on a brake pedal of the driver's vehicle when brake lamps of the preceding vehicle are activated. Through a comparison of event-related potentials between the two experimental conditions of a travel (high-attention condition) during which the preceding vehicle applies sudden brakes and a travel during which the preceding vehicle does not apply sudden brakes (low-attention condition), it reports that the amplitude of P300 of the event-related potential increases under the high-attention condition.

However, the conventional technique described in Japanese Laid-Open Patent Publication No. 2004-178367 is based on the assumption that attention is not being paid to anywhere that the line of sight is not directed, and therefore cannot accurately determine the amount of attention of the peripheral visual region of the driver.

This will be described by taking an actual driving scene as an example. While monitoring a vehicle that is traveling ahead in his or her central visual region, a driver is simultaneously detecting the motions of flanking vehicles and pedestrians in his or her peripheral visual field. As a result, the driver determines the direction of his or her line of sight in accordance with the vehicle situation in the front as well as the neighboring situation. Therefore, with the conventional technique, it is difficult to cope with the case where the line of sight is being directed to the front while also paying attention to the peripheral visual region, for example.

Moreover, in the technique described in Japanese Laid-Open Patent Publication No. 2002-127780, since a brake response time with respect to a sudden deceleration of a preceding vehicle or the like is used, the derived degree of concentration on driving is limited to the front of the driver's vehicle, i.e., the central visual region of the driver. In an actual driving scene, it is very rarely the case that a response to an event occurring in the peripheral visual region of a driver is straightforwardly manifested in behavior such as braking. Therefore, with the conventional technique utilizing the manner in which the driver's vehicle is operated, the amount of attention of the driver to the peripheral visual region cannot be determined with a good accuracy.

Furthermore, in a conventional study which is described in Non-Patent Document 1, an event-related potential (ERP) with respect to activation of the brake lamps of a preceding vehicle is similarly used. Therefore, the amount of driving attention being measured is limited to that pertaining to the central visual region of the driver, and it is impossible to measure the amount of attention to the peripheral visual region.

SUMMARY OF THE INVENTION

The present invention has been made in view of the aforementioned problems, and an objective thereof is to, even when a driver is not directing his or her line of sight to objects in the surroundings, determine the amount of attention of the driver to the peripheral visual region and provide safe driving assistance in accordance with the result of determination.

A driving attention amount determination apparatus according to the present invention comprises: an electroencephalogram measurement section for measuring an electroencephalogram signal of a driver; a central stimulation presentation section for presenting a visual stimulation in a central visual field of the driver; a peripheral stimulation presentation section for presenting a visual stimulation in a peripheral visual field of the driver; a threshold setting section for setting a determination threshold for attention amount determination from a distribution of amplitude of an event-related potential in the electroencephalogram signal based on a point of presenting the stimulation in the central visual field as a starting point; and an attention amount determination section for determining an amount of attention through a comparison between the determination threshold and an amplitude of an event-related potential in the electroencephalogram signal based on a point of presenting the stimulation in the peripheral visual field as a starting point.

The amplitude of an event-related potential based on the point of presenting the stimulation in the central visual field as a starting point may be an amplitude of a P300 which is a positive component in a zone from 300 milliseconds to 600 milliseconds based on a point of presenting a visual stimulation in the central visual field as a starting point; and the amplitude of an event-related potential based on the point of presenting the stimulation in the peripheral visual field as a starting point may be an amplitude of a P300 which is a positive component in a zone from 300 milliseconds to 600 milliseconds based on a point of presenting a visual stimulation in the peripheral visual field as a starting point.

When the central stimulation presentation section has presented a plurality of stimulations in the central visual field, as the determination threshold, the threshold determination section may set a median of P300's respectively based on the point of presenting of each stimulation in the central visual field as a starting point.

The attention amount determination section may determine a stimulation overlooked by the driver, through a comparison between the determination threshold and an amplitude of P300 of an event-related potential based on the point of presenting the stimulation in the peripheral visual field as a starting point.

The attention amount determination section may compare the determination threshold and the amplitude value of an event-related potential based on the point of presenting the stimulation in the peripheral visual field as a starting point, and if the amplitude value is equal to or greater than the determination threshold, determine that the amount of attention is high, and if the amplitude value is smaller than the determination threshold, determine that the amount of attention is low.

Another driving attention amount determination apparatus according to the present invention comprises: an imaging section for imaging a vehicle front; a stimulation detection section for detecting a stimulation contained in a video captured by the imaging section and a time point of occurrence of the stimulation, and detecting whether a position of occurrence of the stimulation in the video is in a central visual region or a peripheral visual region of a driver; an electroencephalogram measurement section for measuring an electroencephalogram signal of the driver; a threshold setting section for setting a determination threshold for attention amount determination from a distribution of amplitude of an event-related potential in the electroencephalogram signal based on a point of presenting a stimulation in the central visual region as a starting point; and an attention amount determination section for determining an amount of attention through a comparison between the determination threshold and an amplitude of an event-related potential in the electroencephalogram signal based on a point of presenting a stimulation in the peripheral visual region as a starting point.

The driving attention amount determination apparatus may further comprise a line-of-sight measurement section for measuring a line of sight of the driver, wherein the stimulation detection section detects whether the stimulation is contained in the central visual region or the peripheral visual region of the driver in accordance with the line of sight of the driver as detected by the line-of-sight measurement section at the time point of occurrence of the stimulation.

The driving attention amount determination apparatus may further comprise: a storage section for storing P300 amplitudes of an event-related potential of the driver generated by the driver in the past in response to stimulations presented by the peripheral stimulation presentation section; and a start threshold setting section for extracting two peaks contained in the stored distribution of P300 amplitudes, and setting the determination threshold by utilizing the two peaks.

The start threshold setting section may set a median of the two peaks as the determination threshold.

A method of driving attention amount determination according to the present invention comprises: an electroencephalogram measurement step of measuring an electroencephalogram signal of a driver; a central stimulation presenting step of presenting a visual stimulation in a central visual field of the driver; a peripheral stimulation presenting step of presenting a visual stimulation in a peripheral visual field of the driver; a threshold setting step of setting a determination threshold for attention amount determination from a distribution of amplitude of an event-related potential in the electroencephalogram signal based on a point of presenting the stimulation in the central visual field as a starting point; and an attention amount determining step of determining an amount of attention through a comparison between the determination threshold and an amplitude of an event-related potential in the electroencephalogram signal based on a point of presenting the stimulation in the peripheral visual field as a starting point.

The amplitude of an event-related potential based on the point of presenting the stimulation in the central visual field as a starting point may be an amplitude of a P300 which is a positive component in a zone from 300 milliseconds to 600 milliseconds based on a point of presenting a visual stimulation in the central visual field as a starting point; and the amplitude of an event-related potential based on the point of presenting the stimulation in the peripheral visual field as a starting point may be an amplitude of a P300 which is a positive component in a zone from 300 milliseconds to 600 milliseconds based on a point of presenting a visual stimulation in the peripheral visual field as a starting point.

The attention amount determining step may compare the determination threshold and the amplitude value of an event-related potential based on the point of presenting the stimulation in the peripheral visual field as a starting point, and if the amplitude value is equal to or greater than the determination threshold, determine that the amount of attention is high, and if the amplitude value is smaller than the determination threshold, determine that the amount of attention is low.

A computer program according to the present invention is a computer program for determining an amount of attention which, by being executed by a computer, causes the computer to execute: a step of receiving a measured electroencephalogram signal of a driver; a central stimulation presenting step of presenting a visual stimulation in a central visual field of the driver; a peripheral stimulation presenting step of presenting a visual stimulation in a peripheral visual field of the driver; a threshold setting step of setting a determination threshold for attention amount determination from a distribution of amplitude of an event-related potential in the electroencephalogram signal based on a point of presenting the stimulation in the central visual field as a starting point; and an attention amount determining step of determining an amount of attention through a comparison between the determination threshold and an amplitude of an event-related potential in the electroencephalogram signal based on a point of presenting the stimulation in the peripheral visual field as a starting point.

Still another driving attention amount determination apparatus according to the present invention comprises: a central stimulation presentation section for presenting a visual stimulation in a central visual field of the driver; a peripheral stimulation presentation section for presenting a visual stimulation in a peripheral visual field of the driver; a threshold setting section for setting a determination threshold for attention amount determination from a distribution of amplitude of an event-related potential in an electroencephalogram signal of the driver measured by an electroencephalogram measurement section for measuring an electroencephalogram signal based on a point of presenting the stimulation in the central visual field as a starting point; and an attention amount determination section for determining an amount of attention through a comparison between the determination threshold and an amplitude of an event-related potential in the electroencephalogram signal based on a point of presenting the stimulation in the peripheral visual field as a starting point.

Still another driving attention amount determination apparatus according to the present invention is a driving attention amount determination apparatus for receiving data of a stimulation contained in a video of a vehicle front captured by an imaging section, data of a time point of occurrence of the stimulation, and data of a result of detection as to whether a position of occurrence of the stimulation in the video is in a central visual region or a peripheral visual region of a driver, the driving attention amount determination apparatus comprising: a threshold setting section for setting a determination threshold for attention amount determination from a distribution of amplitude of an event-related potential in an electroencephalogram signal based on a point of presenting a stimulation in the central visual region as a starting point, the electroencephalogram signal being measured by an electroencephalogram measurement section for measuring an electroencephalogram signal; and an attention amount determination section for determining an amount of attention through a comparison between the determination threshold and an amplitude of an event-related potential in the electroencephalogram signal based on a point of presenting a stimulation in the peripheral visual region as a starting point.

The attention amount determination section may output data of a result of determination.

The driving attention amount determination apparatus may further comprise a display device for displaying the result of determination which is output from the attention amount determination section.

The driving attention amount determination apparatus may further comprise a storage device for storing data of the result of determination which is output from the attention amount determination section.

According to the present invention, from an electroencephalogram signal measured based on a starting point which is the time point of occurrence of a visual stimulation occurring in a peripheral visual region of a driver, an amount of attention of the driver to the peripheral visual field is determined. By using the electroencephalogram signal, it becomes possible to accurately determine an amount of attention to events that may possibly occur in the peripheral visual field of the driver (e.g., a sudden intrusion of a vehicle or a rushing out of a pedestrian), and based on the result of determination, a change in the state of the driver can be appropriately induced, e.g., by attention calling.

Other features, elements, processes, steps, characteristics and advantages of the present invention will become more apparent from the following detailed description of preferred embodiments of the present invention with reference to the attached drawings.

Figure 13:
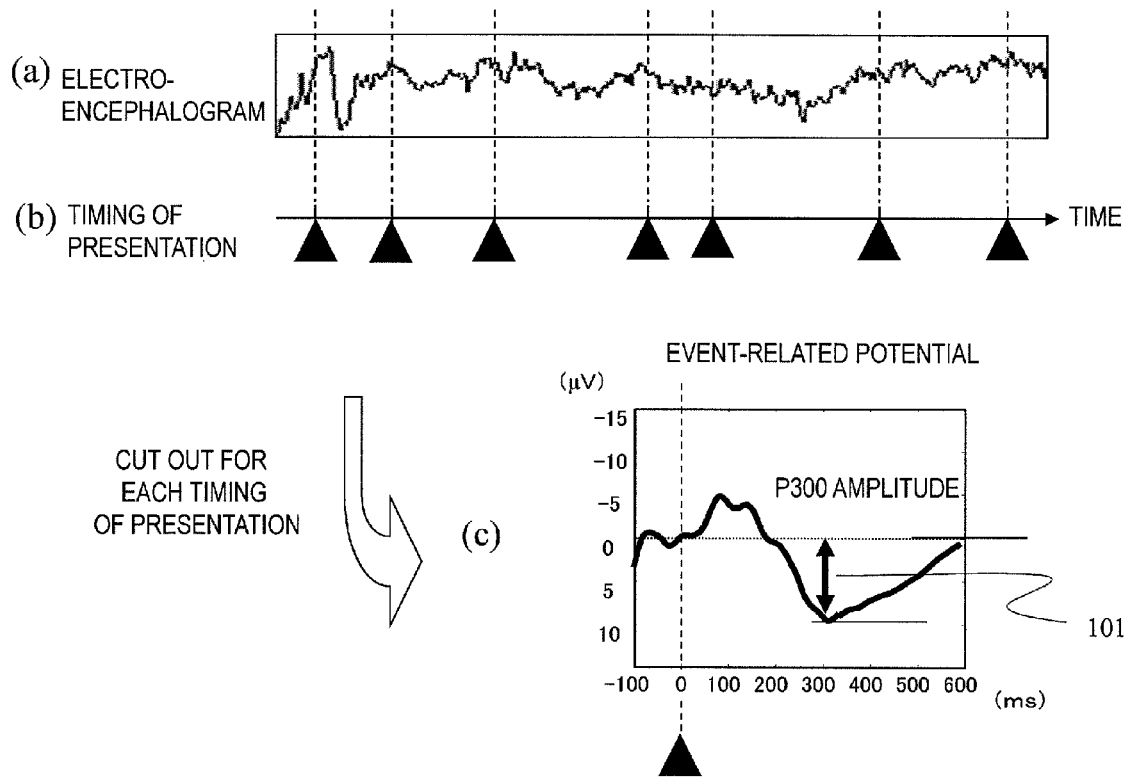

Portions (a) to (c) of FIG. 13 are diagrams showing an exemplary processing by the threshold setting section 40.

Figure 14:
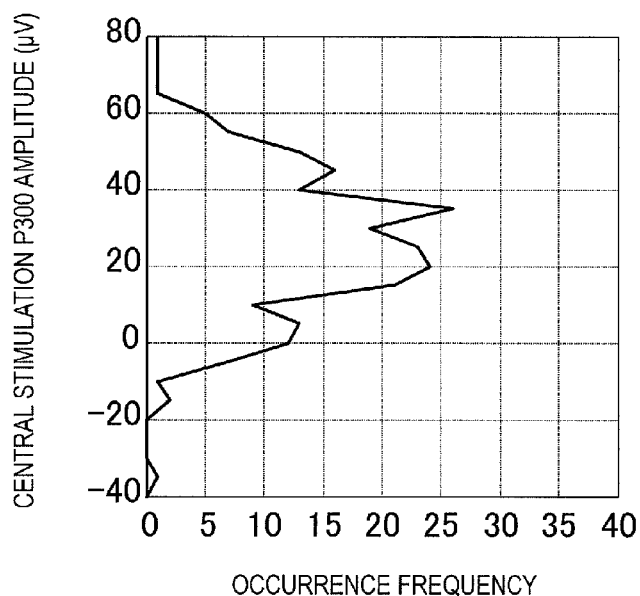

FIG. 14 is a diagram showing an exemplary P300 distribution analyzed in an experiment.

Figure 15:
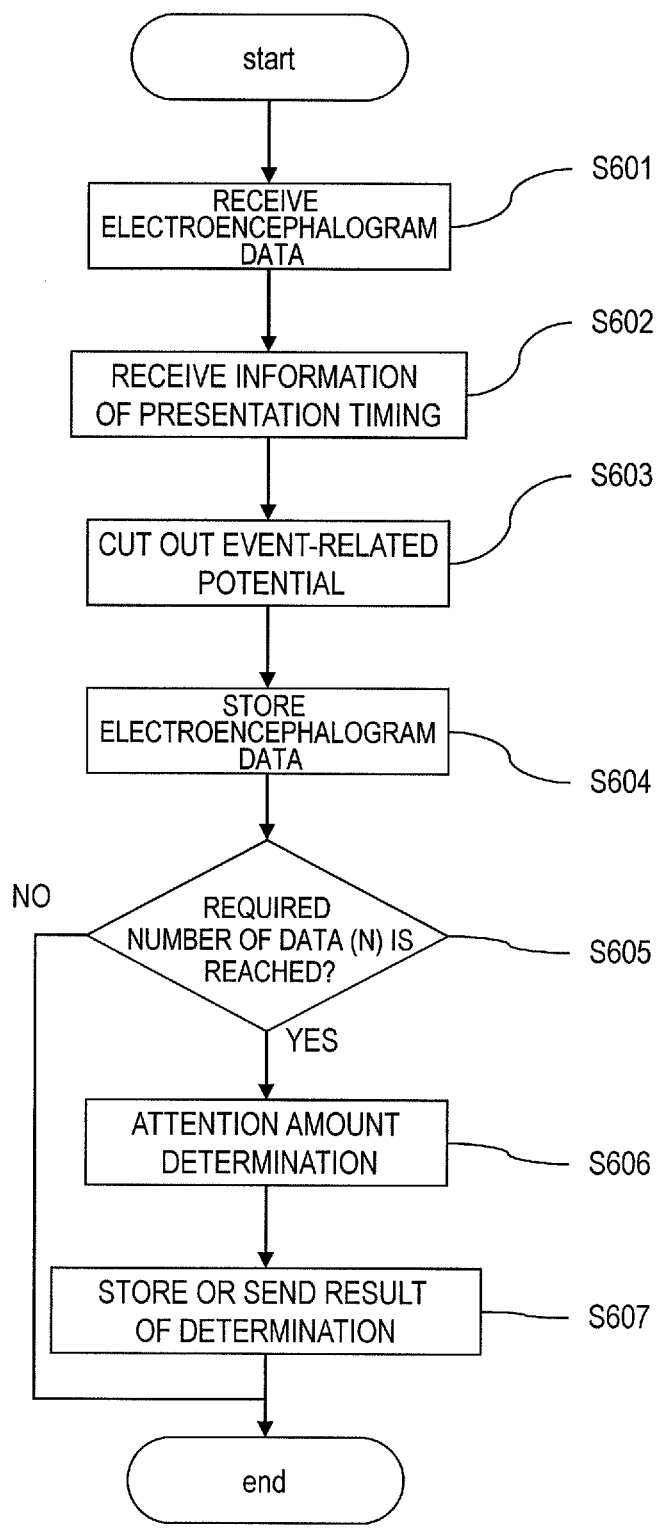

FIG. 15 is a flowchart showing a flow of processes at step S60 (FIG. 10) which is conducted by an attention amount determination section 60.

Figures 16, 17:
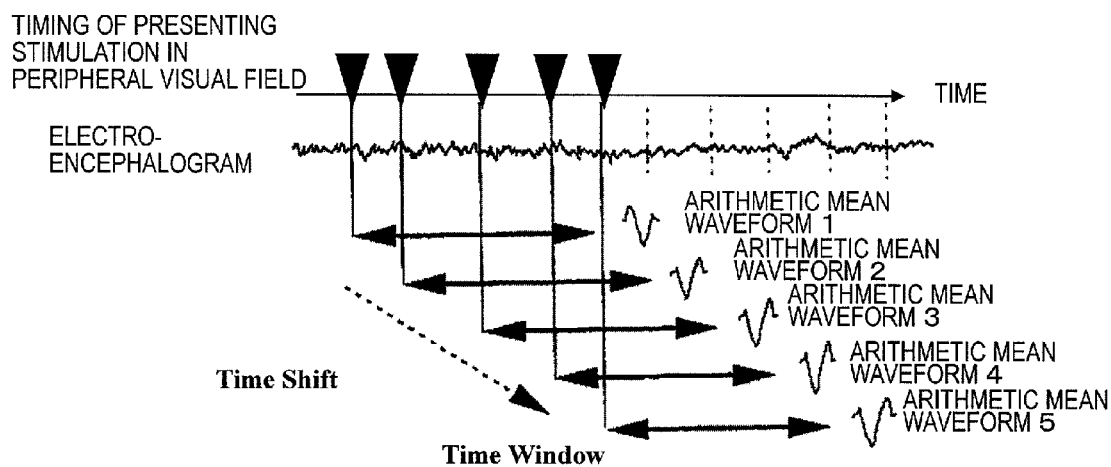

FIG. 16 is a diagram showing arithmetic mean waveforms 1 to 5 obtained by adopting a time sliding approach.

FIG. 17 is a diagram showing examples of information that are stored.

Figure 18A:
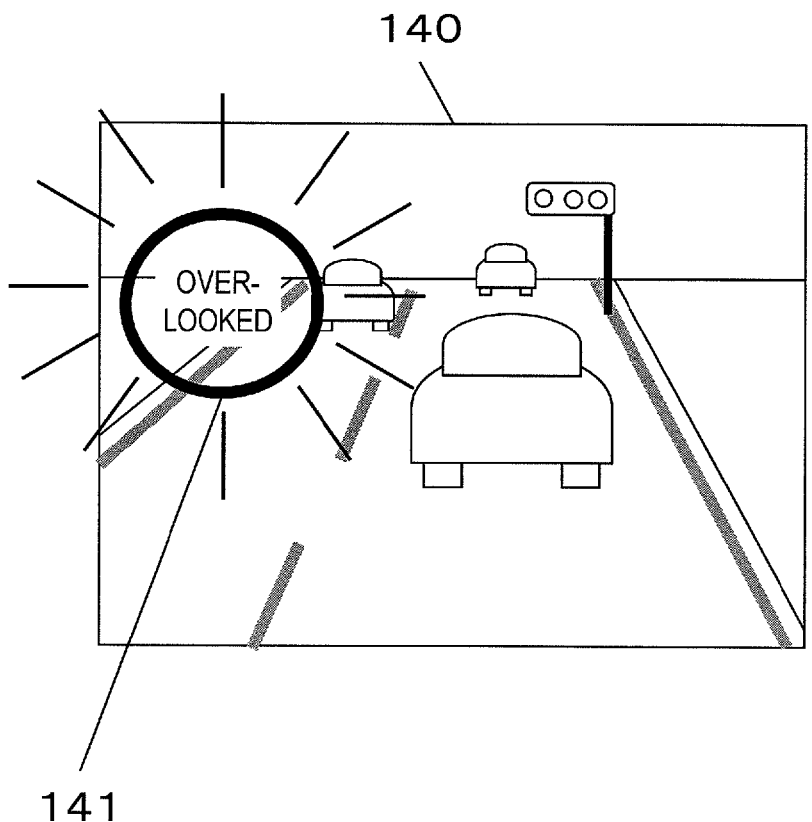

FIG. 18A is a diagram showing an exemplary indication of an alarm.

Figure 18B:
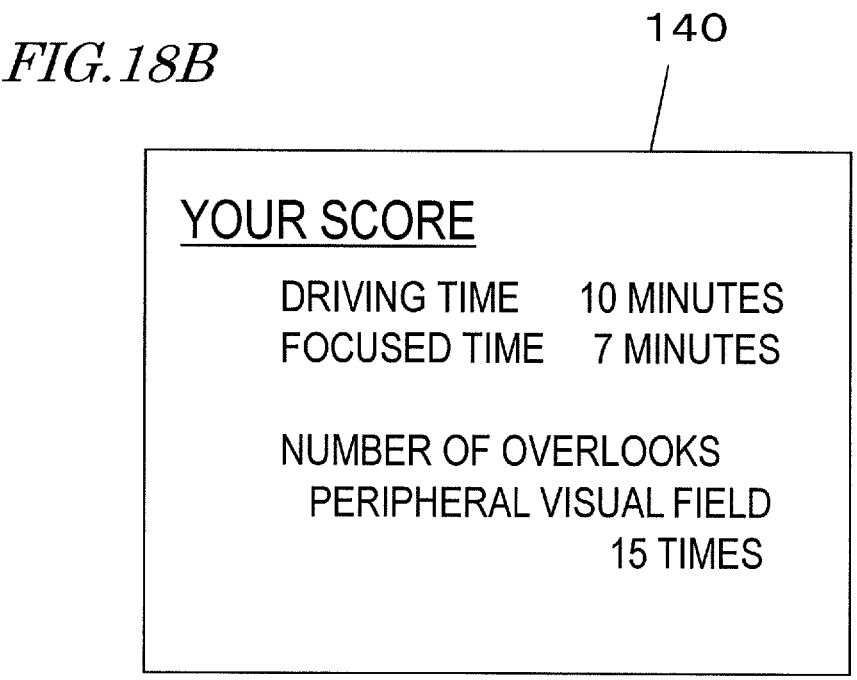

FIG. 18B is a diagram showing an exemplary indication of a driving score.

Figures 19, 20:
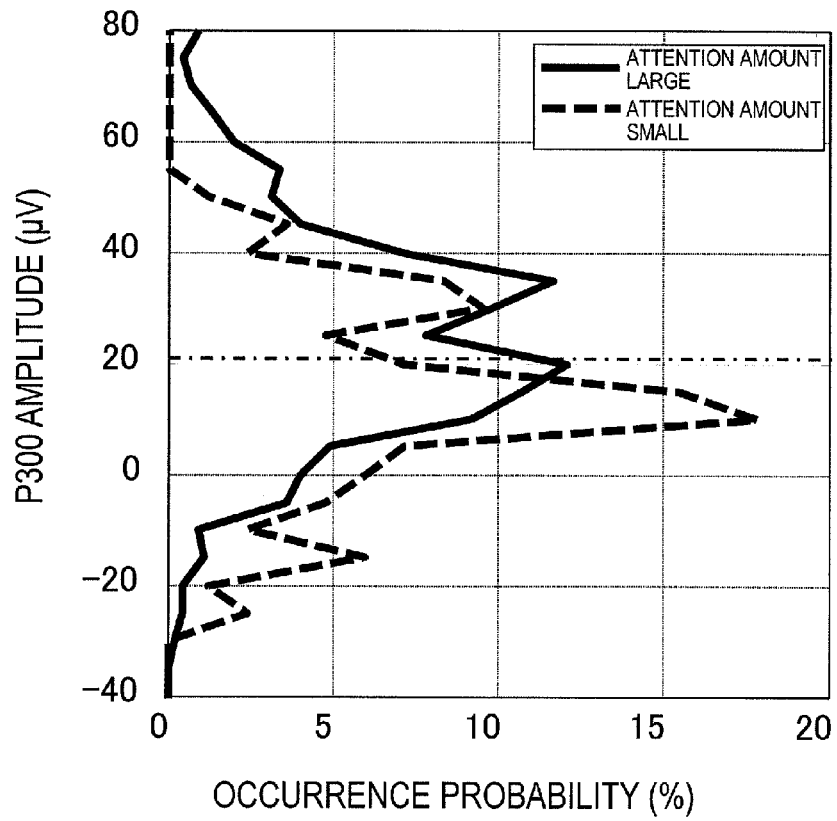

FIG. 19 is a diagram showing a P300 distribution of responses to peripheral stimulations in an experiment.

FIG. 20 is a diagram showing distinction rate results when attention amount determination is performed by the technique of the present invention.

Figure 21:
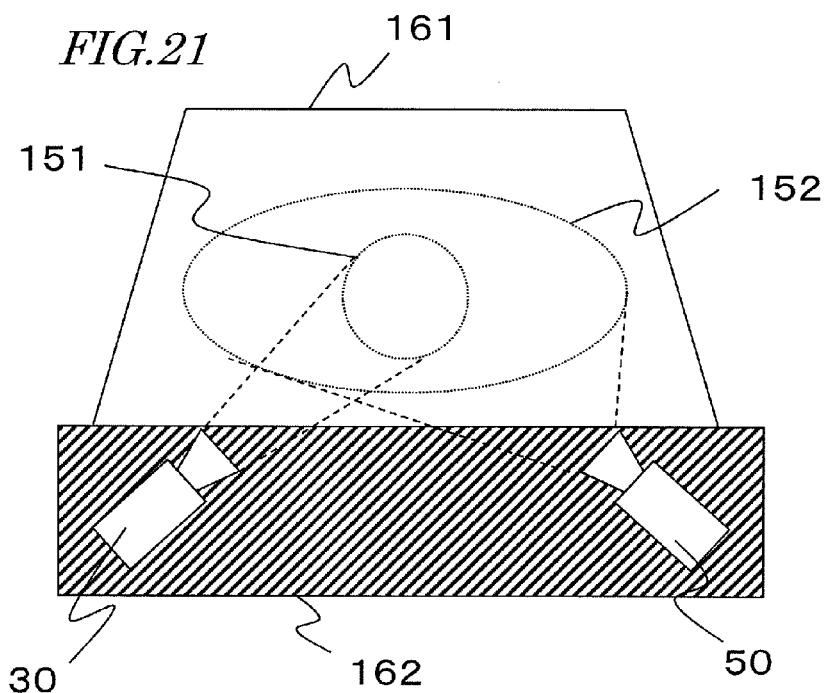

FIG. 21 is a diagram showing an exemplary construction of a central stimulation presentation section 30 and a peripheral stimulation presentation section 50.

Figure 22:
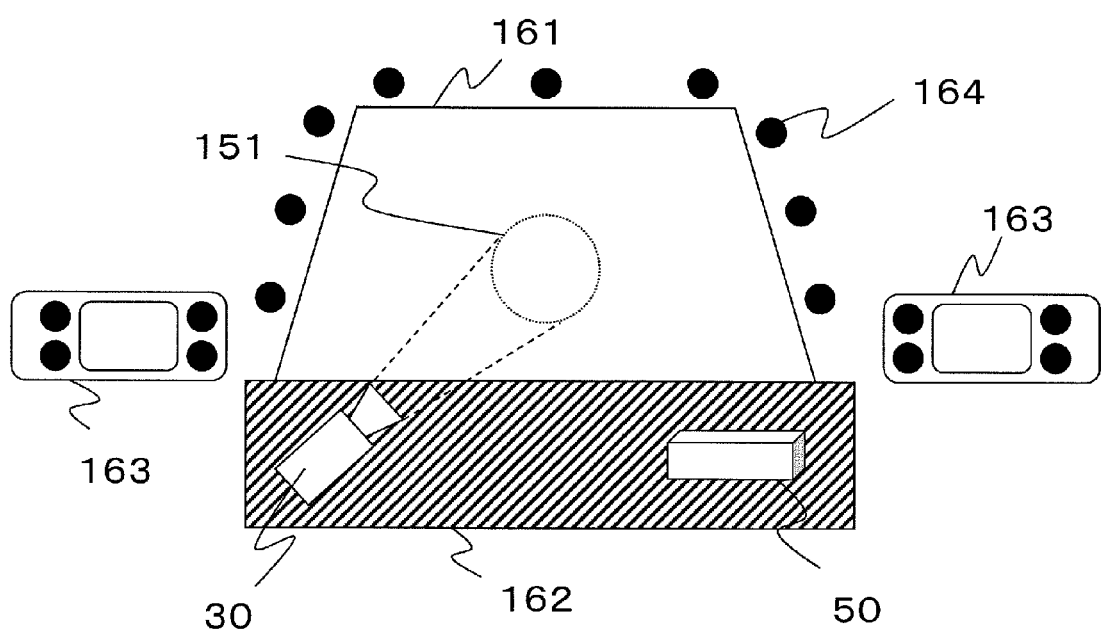

FIG. 22 is a diagram showing an example where no projector is employed for presenting a peripheral stimulation.

Figure 23:
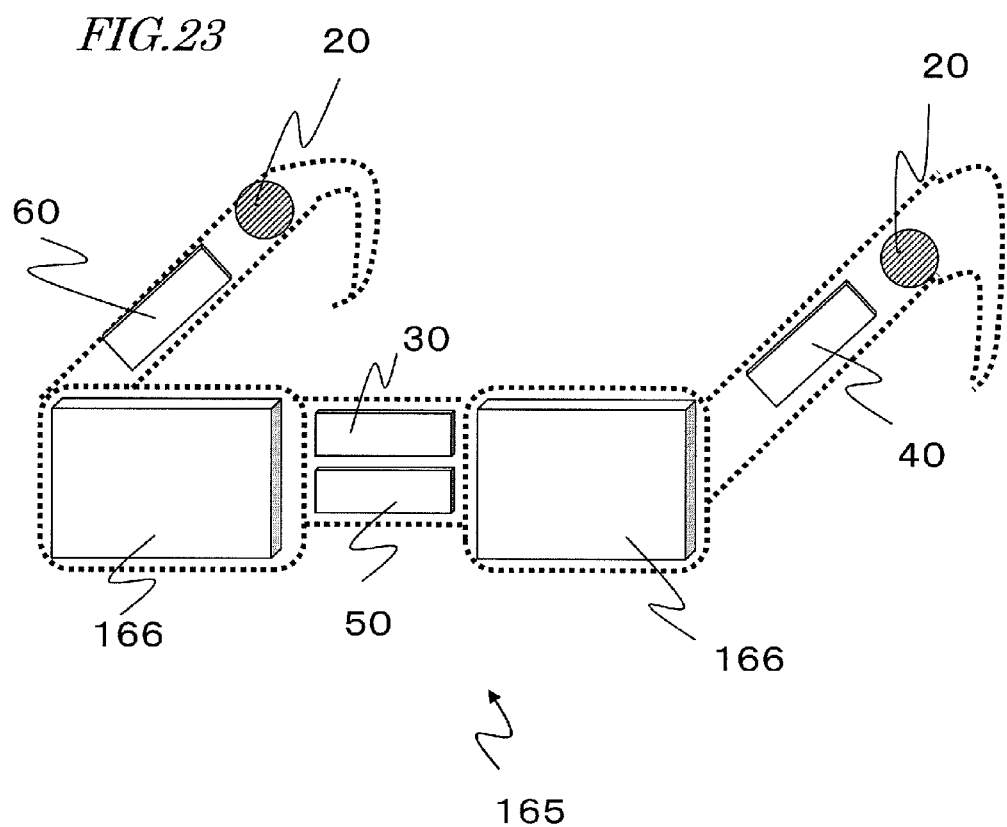

FIG. 23 is a diagram showing an example where the construction of the present embodiment is incorporated in an HMD 165.

Figure 24:
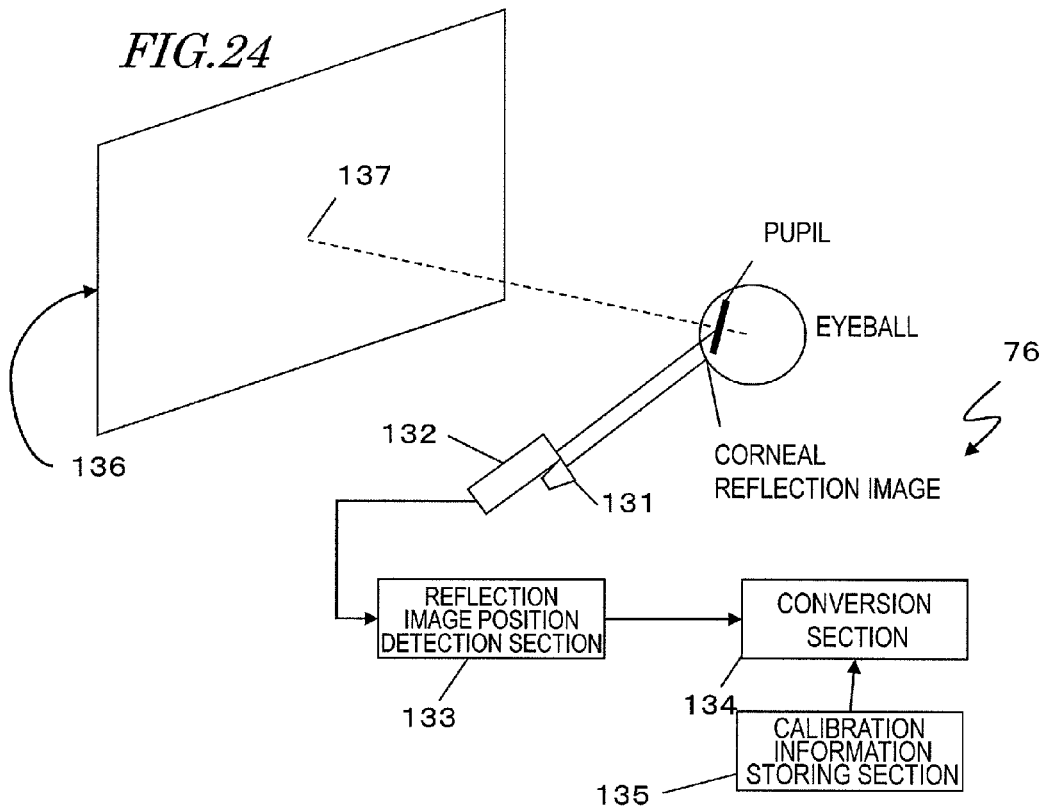

FIG. 24 is a diagram showing an example of a line-of-sight measurement section 76.

Figure 25:
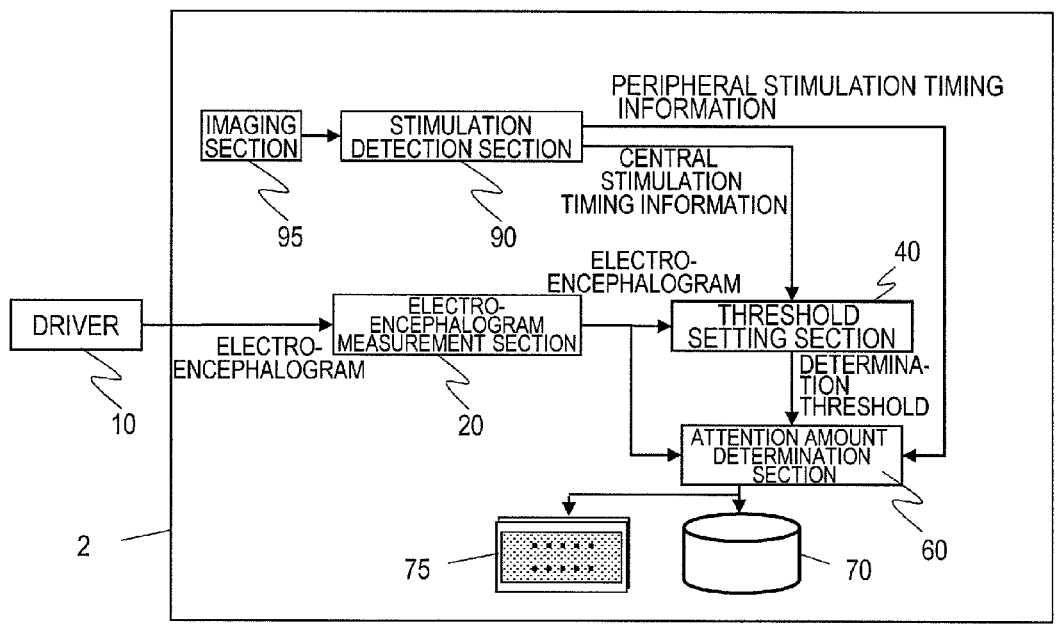

FIG. 25 is a diagram showing a block construction of a driving attention amount determination apparatus 2 according to Embodiment 2, in which an imaging section 95 is provided.

Figure 26:
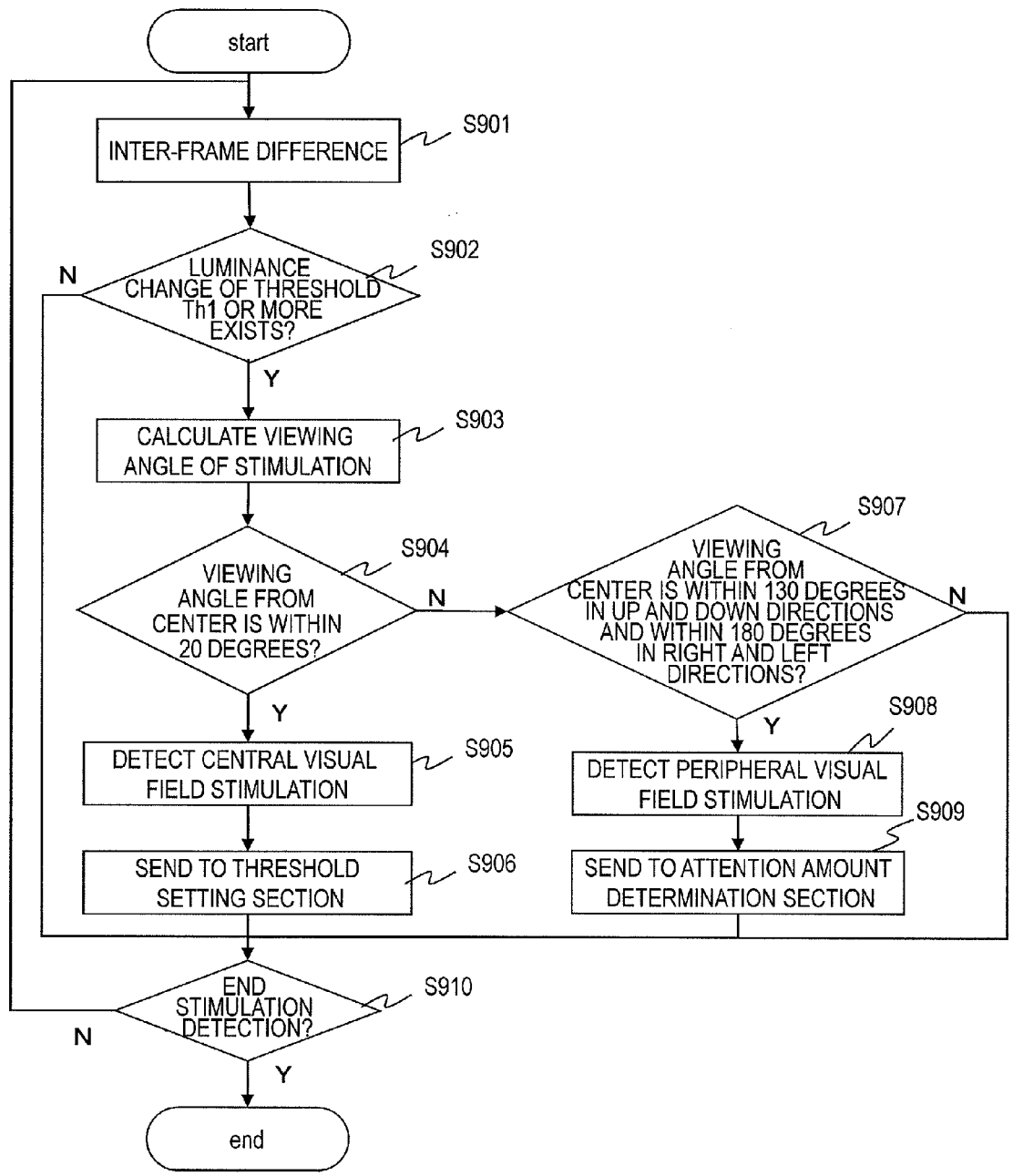

FIG. 26 is a flowchart showing the details of processing by a stimulation detection section 90.

Figure 27:
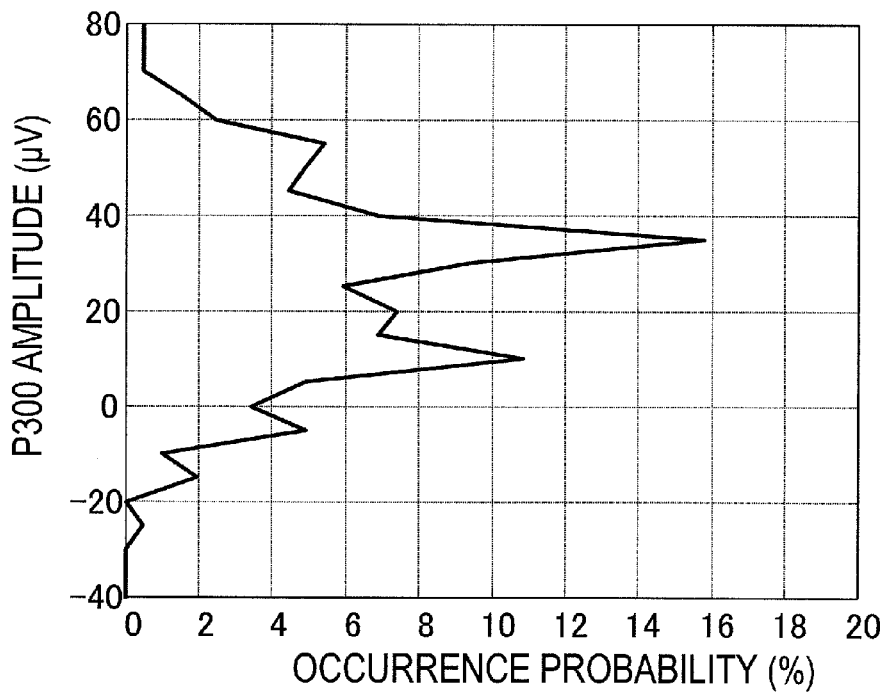

FIG. 27 is a diagram showing a P300 distribution for peripheral stimulations in an experiment.

Figure 28:
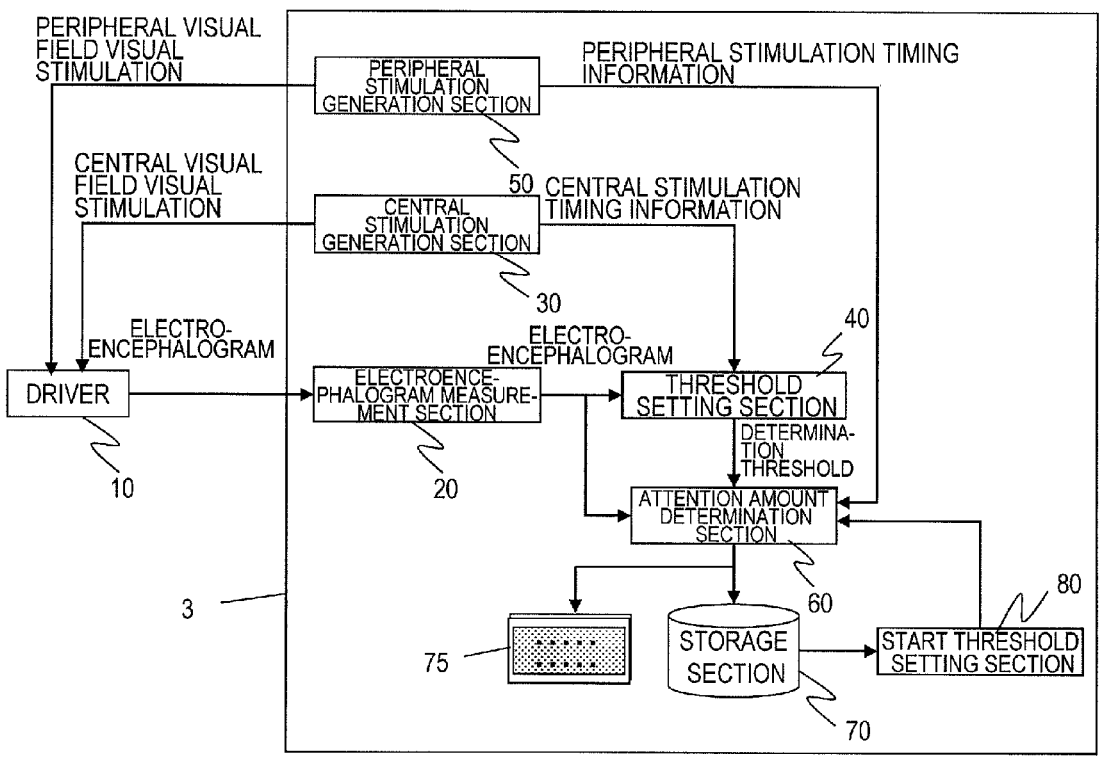

FIG. 28 is a diagram showing a block construction of an attention amount determination apparatus 3 according to Embodiment 3.

Figure 29:
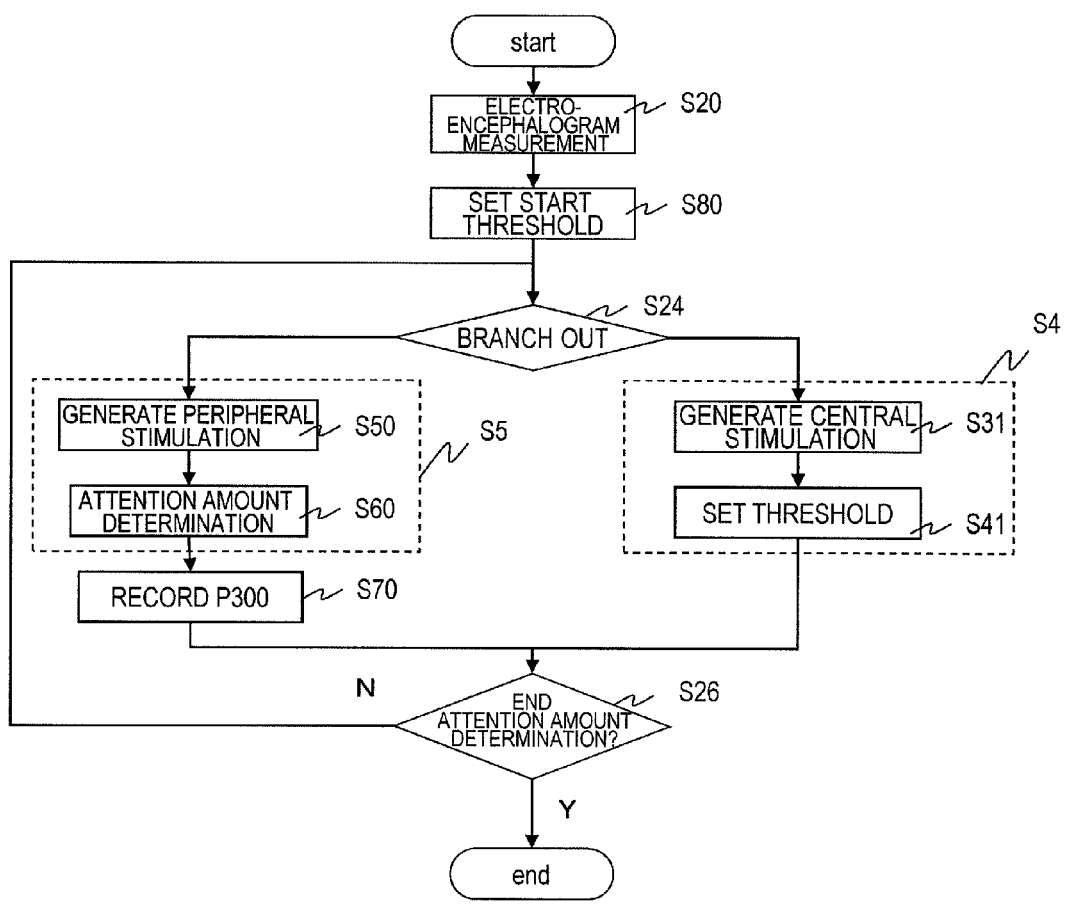

FIG. 29 is a flowchart of processes by the attention amount determination apparatus 3 according to Embodiment 3.

Figures 30, 31:
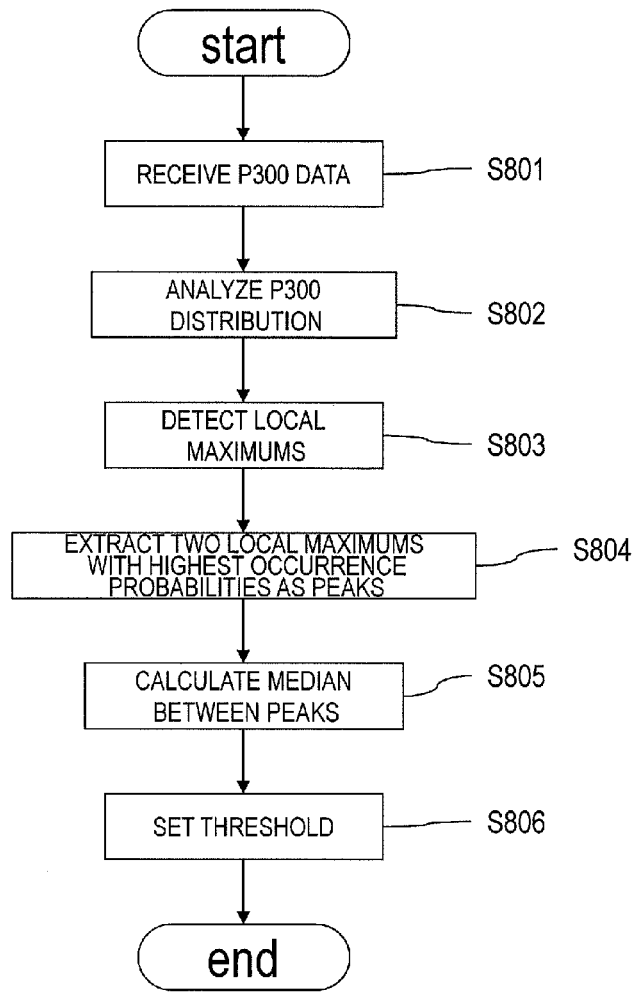

FIG. 30 is a flowchart showing a flow of processes at step S80 which is conducted by a start threshold setting section 80.

FIG. 31 is a diagram showing an exemplary format of received data.

FIG. 32A is a diagram showing an example of a local maximum to be extracted.

FIG. 32B is a diagram showing an example of extracted distribution peaks.

FIG. 33 is a diagram showing a result of making a determination by utilizing a recorded peripheral stimulation-P300 distribution.

DETAILED DESCRIPTION OF PREFERRED EMBODIMENTS

First, the terms "event-related potential" and "latency" used in the present specification will be described.

An "event-related potential" is a portion of an electroencephalogram, and refers to a transient potential fluctuation in the brain which occurs in temporal relationship with an external or internal event. For example, temporal changes in the electroencephalographic potential may be measured as an electroencephalogram signal, and an event-related potential can be obtained from that electroencephalogram signal. Specifically, it may be defined by the polarity of a peak (a local maximum or a local minimum) of the electroencephalogram signal waveform, the latency of the peak, or temporal changes in the amplitude or latency of the waveform of the electroencephalogram signal, etc.

"Latency" represents an amount of time until a local maximum or local minimum of the event-related potential of interest appears, since the point in time of presenting a stimulation as a starting point.

Generally speaking, a "positive component" refers to a potential which is greater than 0 μV. Generally speaking, a "negative component" refers to a potential which is smaller than 0 μV.

According to Table 1 on p. 30 of "JISHOUKANRENDENI (ERP) MANYUARU—P300 WO CHUSHINNI (or "Event-Related Potential (ERP) Manual—mainly concerning P300"), edited by Kimitaka KAGA et al., Shinohara Shuppan Shinsha, 1995)", generally speaking, there are 30 milliseconds to 50 milliseconds of differences (shifts) in event-related potential waveform between individuals. Therefore, the terms "about X milliseconds" and "near X milliseconds" mean that a breadth of 30 milliseconds to 50 milliseconds may exist before or after X milliseconds (e.g., 300 milliseconds±30 milliseconds, 600 milliseconds±50 milliseconds). In the following description, the breadth is assumed to be 50 milliseconds.

The inventors have conducted an experiment to see what sort of differences may exist between an event-related potential with respect to a stimulation occurring in the central visual region and an event-related potential with respect to a stimulation occurring in the peripheral visual region. As a result, the inventors have found characteristics such that the amplitude of an event-related potential with respect to a stimulation occurring in the peripheral visual region from 300 milliseconds to 600 milliseconds greatly changes depending on whether the amount of attention is large or small.

First, the experiment details and the findings obtained from the experimental results will be describe detect. Thereafter, techniques utilizing these findings will be discussed, and problems which may newly occur will be described.

A total of 4 test subjects were involved, including one male and three females, with an average age of 21±1.5 years. The experimental details will be described with reference to FIG. 1.

The inventors performed the experiment by a dual task method, in which each test subject was asked to perform two tasks concurrently. The first task was a central task 111 of counting to oneself a number of times that symbols (○/Δ/□/x) presented on a screen center in a monitor 2 of FIG. 1 were switched. The second task was a peripheral task 112, in which lamps in the screen periphery were flickered in random order, and the test subject was supposed to press a button at hand as soon as noticing a flicker. The test subject was instructed to always keep his or her line of sight at the screen center. Thus, by having each test subject simultaneously perform the two tasks at the screen center and in the periphery, it is possible to examine how much attention is being paid to the periphery while also paying attention to the screen center. In order to allow the test subject to have a peripheral visual field, three 20" display monitors 1 to 3 were placed side by side, with a distance of 60 cm between the test subject and the screen. Although failing to mock a vehicle-driving environment, this experiment can be construed as an abstracted experiment for examining how quickly a change in the periphery can be noticed while watching the fixation point.

Figure 2:
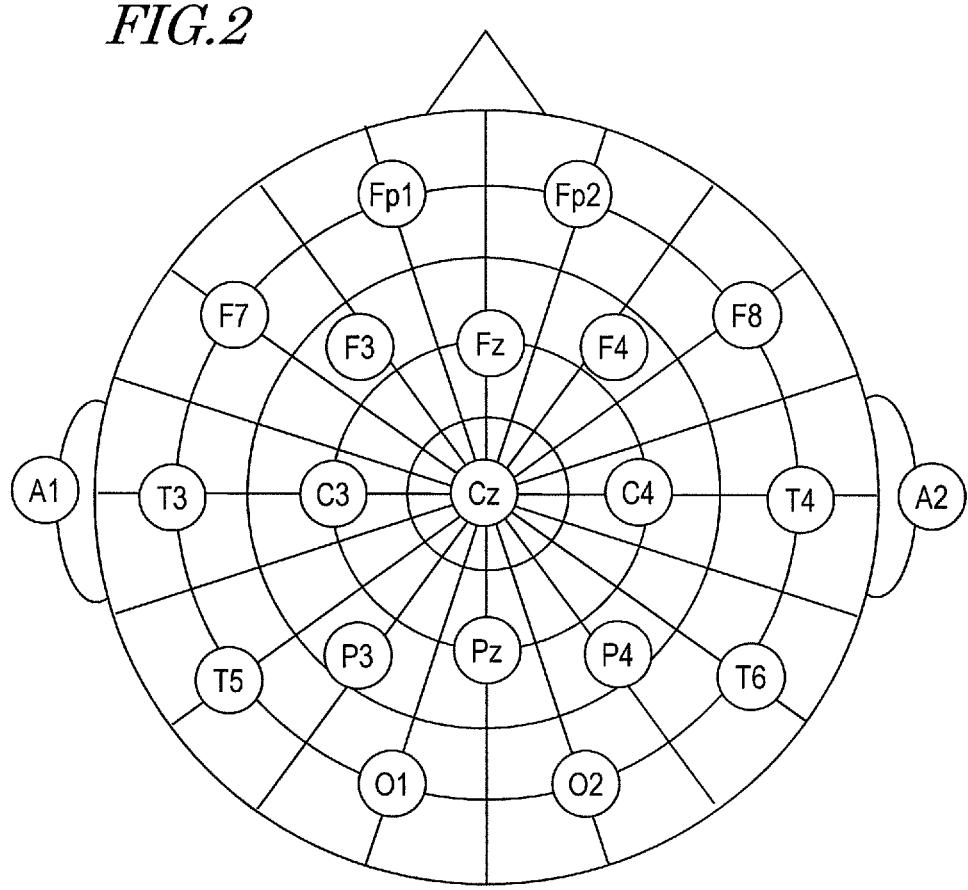
FIG. 2 is a diagram showing electrode positions in the International 10-20 system.

Moreover, each test subject was asked to wear an electroencephalograph (manufactured by TEAC Corporation, Polymate AP-1124). The International 10-20 electrode system was adopted for the electrode positioning. FIG. 2 shows the electrode positioning of the International 10-20 electrode system. A recording electrode was at Pz (median parietal), a reference electrode at A1 (right earlobe), and a ground electrode at the metopic. Electroencephalogram data which was measured with a sampling frequency of 200 Hz and a time constant of 3 seconds was subjected to a bandpass filtering process from 1 to 6 Hz. Electroencephalogram data from −100 milliseconds to 600 milliseconds was cut out based on the flickering of a peripheral lamp as a starting point, and a baseline correction was performed with respect to an average potential from −100 milliseconds to 0 milliseconds.

Figure 3:
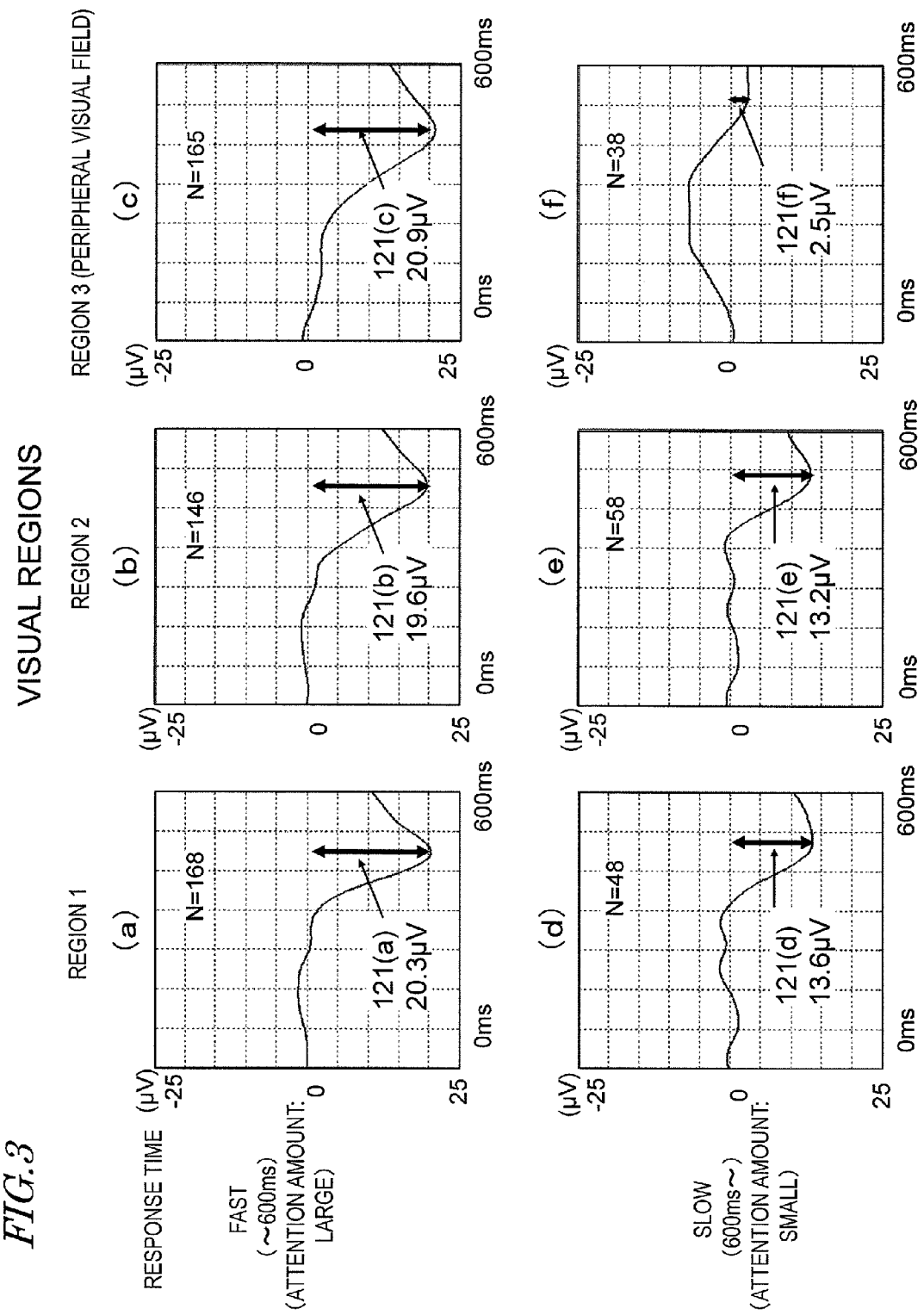
FIG. 3 is a diagram showing arithmetic mean waveforms for different visual regions and response times.

FIG. 3 shows arithmetic mean waveforms of all test subjects, with respect to different combinations of first and second conditions, showing electroencephalogram data after the aforementioned processing was performed.

Figure 1:
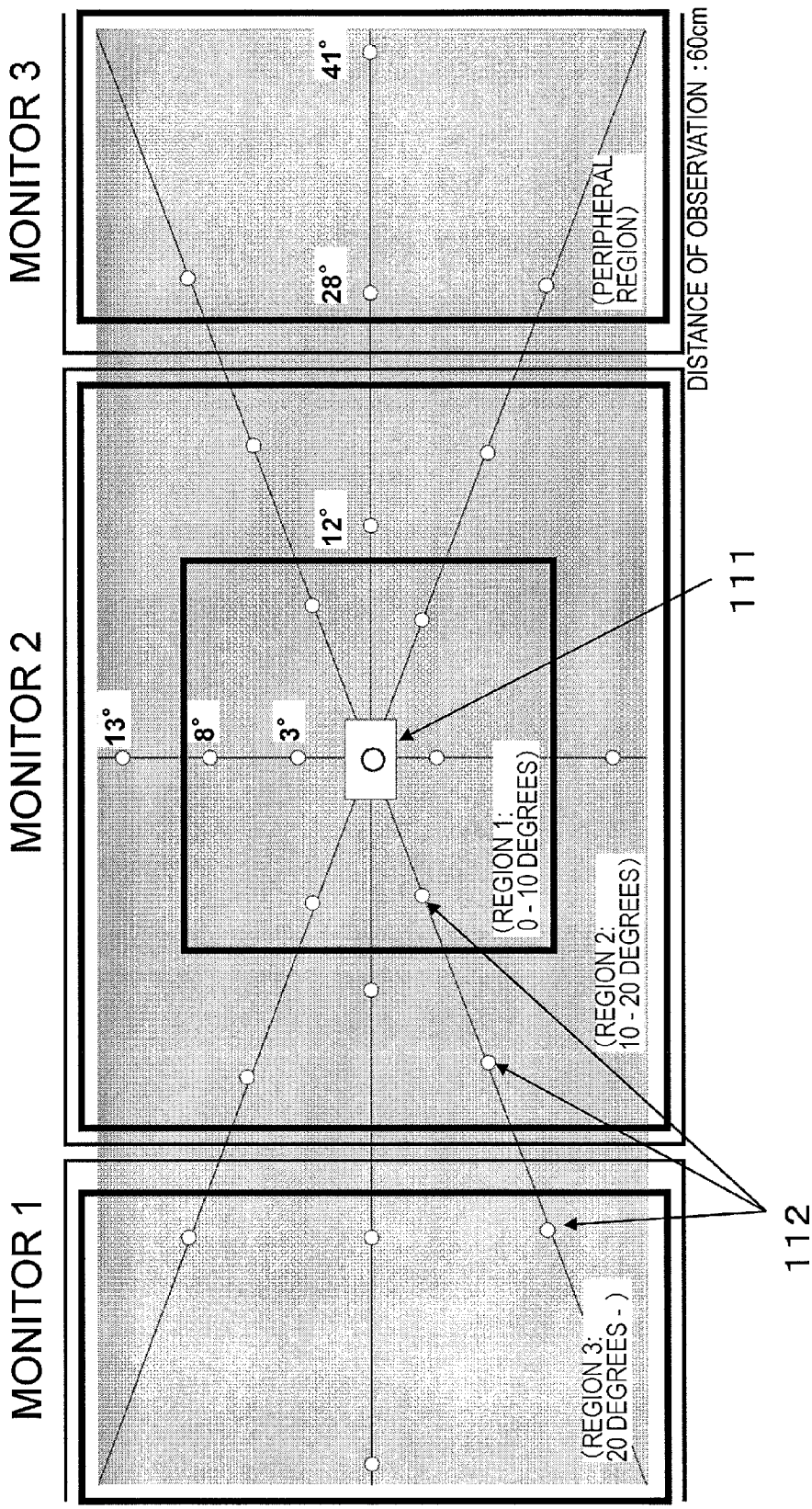
FIG. 1 is a diagram showing screens presented in an experiment conducted by the inventors.

The first condition concerns a classification with respect to the visual regions. In this experiment, the classification was made as shown in FIG. 1: region 1 was defined as spanning a viewing angle (an angle at which a line connecting the center position of an eye of a test subject and a fixation point at the screen center intersects a line connecting the center position of the eye of the test subject and a flicker lamp) of equal to or greater than 0° but less than 10°; region 2 was defined as spanning a viewing angle of equal to or greater than 10° but less than 20°; and region 3 was defined as spanning a viewing angle of 20° or more.

Now, the visual regions will be described.

Figure 4:
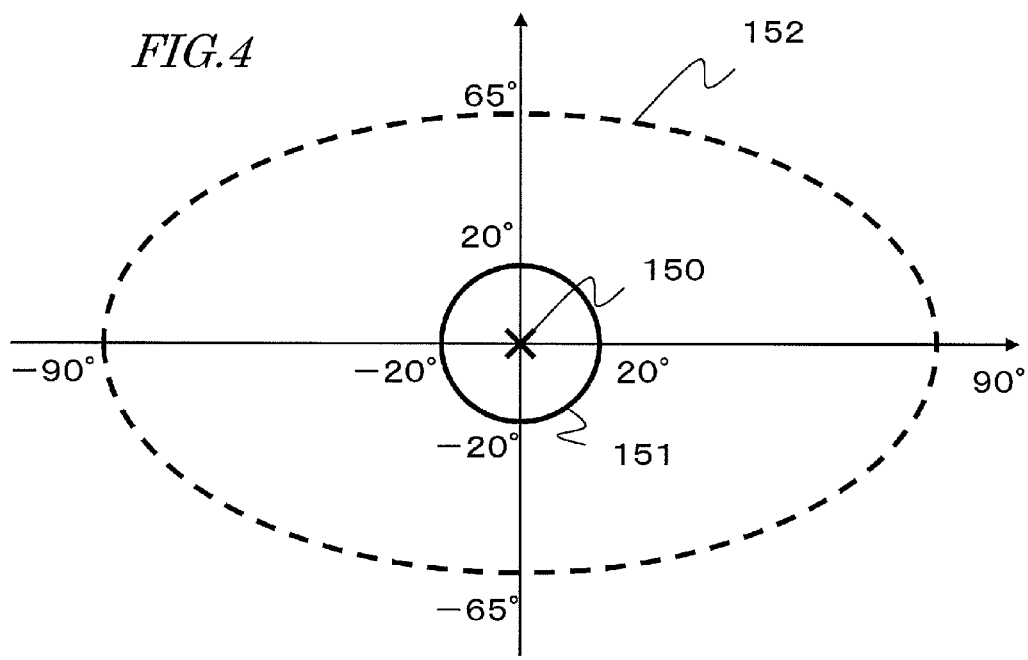
FIG. 4 is a diagram schematically showing a central visual region 151 and a peripheral visual region 152.

Visual regions are generally divided into two, i.e., the central visual region and the peripheral visual region. FIG. 4 schematically shows a central visual region 151 and a peripheral visual region 152. In this diagram, an intersection between the horizontal axis and the vertical axis is at a line of sight (fixation point) 150.

Generally speaking, with either eye, the human field of vision spans a range of about 130 degrees in up and down directions and about 180 degrees in right and left directions, such that an image in this range is projected onto the retina. However, the retina sensitivity is only high in the central portion, while the resolution (which is the power of discerning details) rapidly decreases away from the center.

In other words, the neighborhood of the end of the line of sight (fixation point) 150 can be clearly seen, while the surrounding region receives a lower resolution. The region which is relatively clearly grasped around this fixation point is the effective field of vision or the central visual region 151. As described above, the central visual region 151 is a range of 40 degrees centered around the line of sight (Toshiaki MIURA et al., "JIKOTO ANZENNO SHINRIGAKU" (or "Psychology Of Accidents And Safety"), 2007, p131, University of Tokyo Press).

The peripheral visual region 152 is a region outside the central visual region 151. As is known, although in the peripheral visual region 152, it is difficult to recognize the shape and color of an object in detail, but sensitive response occurs with respect to any object that changes in time, e.g., a moving object or flickering light. Within the entire field of vision which is defined by a range of 130 degrees in up and down directions and 180 degrees in right and left directions, the peripheral visual region 152 is a region ranging outside the central visual region 151.

The regions 1 and 2 in FIG. 1 correspond to the central visual region 151 shown in FIG. 4, whereas the region 3 in FIG. 1 corresponds to the peripheral visual region 152 shown in FIG. 4.

The second condition concerns a classification with respect to each test subject's response time regarding a button press. In this experiment, in order to classify the amount of attention (large or small) as an experimental condition, a response time before achieving a button press was used. In physiopsychological experiments, response time is supposed to reflect the amount of attention; for example, in Japanese Laid-Open Patent Publication No. 2002-127780, too, a degree of concentration of attention to driving is calculated by using a brake response time.

In this experiment, a relationship between an electroencephalogram and an amount of attention as an index of button-press response time was analyzed. Among all response times in this experiment, very many samples were found between 400 milliseconds and 600 milliseconds. Therefore, a classification was made into two groups: fast response time, i.e., a state of high attention to the stimulation, where a response was attained within 600 milliseconds; and slow response time, i.e., a state of low attention to the stimulation, where a response was not attained within 600 milliseconds.

In each of the graphs in FIG. 3, the horizontal axis represents time (latency) since the lamp flickering at 0 milliseconds in units of milliseconds, and the vertical axis represents potential in units of μV. A number (N) shown in each graph represents each number of summations.

FIG. 3 indicates that, when the response time is fast, i.e., the amount of attention is large ((a) to (c) in FIG. 3), the amplitude of P300 (which is a positive component with a latency between 300 milliseconds and 600 milliseconds) is large regardless of the visual field. Note that "a latency of 300 milliseconds to 600 milliseconds" means a latency which is no less than 300 milliseconds and no more than 600 milliseconds.

The maximum amplitudes (121(a) to (c)) of P300 in FIGS. 3(a) to (c) are 20.3 μV, 19.6 μV, and 20.9 μV, respectively. On the other hand, when the response time is slow, i.e., the amount of attention is small (FIGS. 3(d) to (f)), the amplitude of P300 is relatively small. It can be seen that a large decrease in the amplitude of P300 occurs in the case of region 3 with a viewing angle of 40° or more (a region which is generally considered as a peripheral visual field) combined with a small attention amount ((f) in FIG. 3). The maximum amplitudes (121(d) to (f)) of P300 in FIGS. 3(d) to (f) are 13.6 μV, 13.2 μV, and 2.5 μV, respectively.

Figure 5:
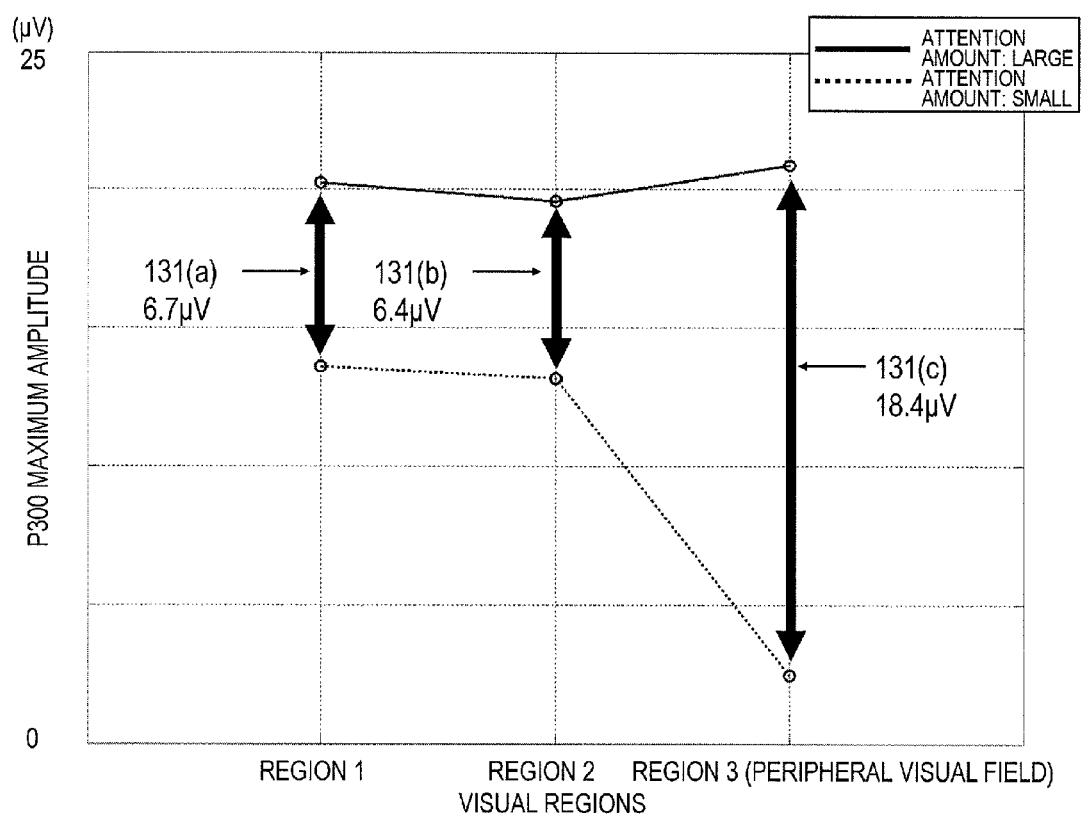
FIG. 5 is a diagram showing P300 maximum amplitude under the respective conditions in FIG. 3.

FIG. 5 shows the maximum amplitudes of a P300 component under the respective conditions of FIG. 3. The visual region (region 1/region 2/region 3) is taken on the horizontal axis, whereas the vertical axis represents potential in units of μV. The solid line represents the case where the amount of attention is large, whereas the dotted line represents the case where the amount of attention is small. In each visual region, the amplitude differences 131(a) to (c) between the case of a large amount of attention and the case of a small amount of attention are 6.7 μV, 6.4 μV, and 18.4 μV, respectively. FIG. 5 also indicates that, in region 3 with a viewing angle of 40° or more (peripheral visual region), considerable amplitude differences exist depending on whether the amount of attention is large or small.

Figure 6:
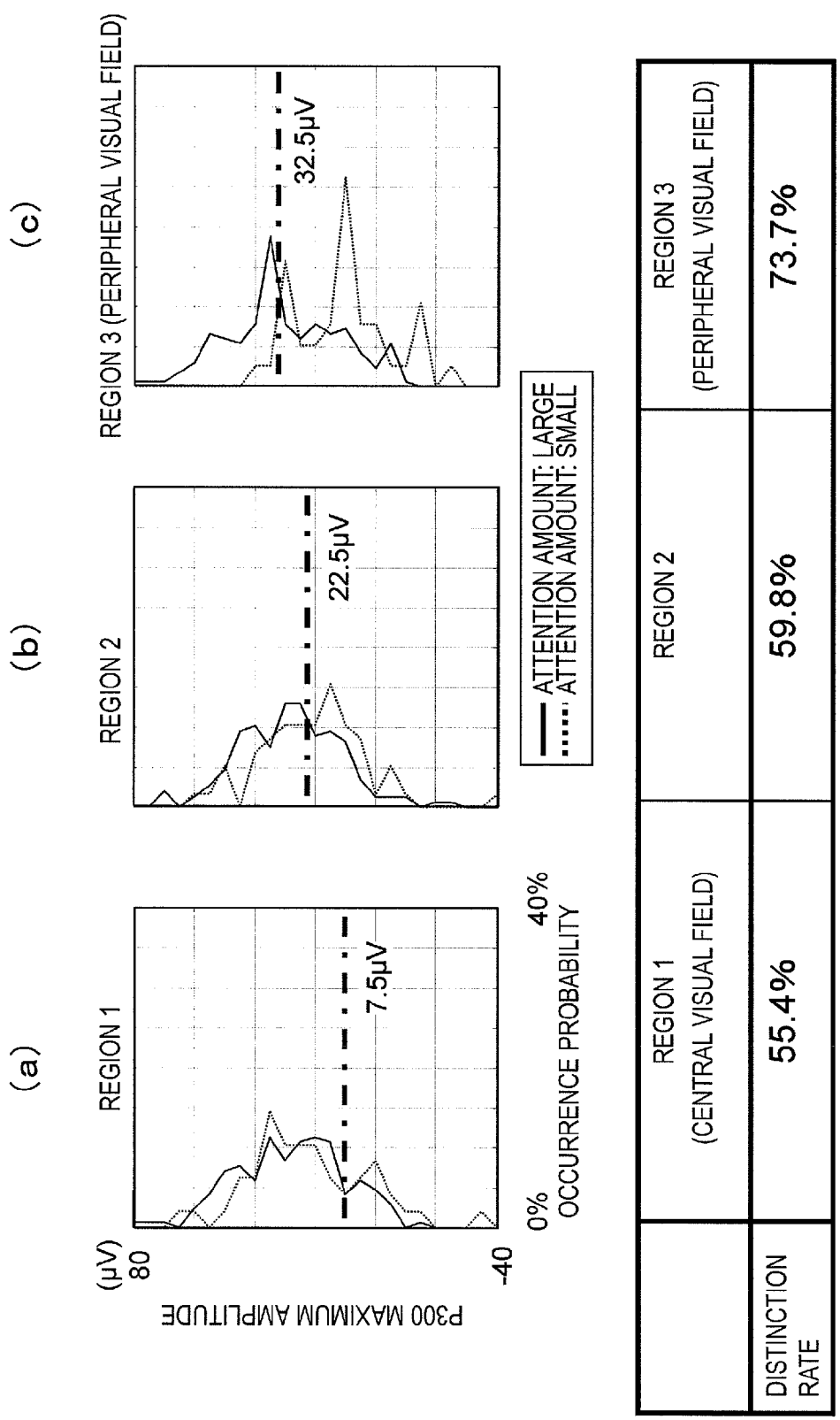
FIG. 6 shows diagrams showing probability distributions of the P300 maximum amplitude in a non-cumulative electroencephalogram and attention amount distinction rates with respect to different visual regions.

FIG. 6 shows probability distributions of the P300 maximum amplitude in a non-cumulative electroencephalogram and attention amount distinction rates with respect to different visual regions. FIG. 6(a) shows a probability distribution for region 1 (central visual region); FIG. 6(b) shows that for region 2; and FIG. 6(c) shows that for region (peripheral visual region). In each graph, the vertical axis represents potential in units of μV, and the horizontal axis represents occurrence probability for the respective amounts of attention in units of %. Under each graph is indicated a distinction rate when making a determination as to whether the amount of attention is large or small in each visual region.

In the method of determining whether the amount of attention is large or small, a threshold value of ERP maximum amplitude that maximizes the distinction rate in each visual region is chosen, and a determination is made based on whether or not the ERP amplitude of each non-cumulative electroencephalogram is equal to or greater than this threshold value. As the threshold value that maximizes the distinction rates, a threshold value is chosen at which a largest average is obtained between the correctness rate of the case where the amount of attention is large and the correctness rate of the case where the amount of attention is small. In the cases of FIGS. 6(a) to (c), the aforementioned threshold values were 7.5 µV, 22.5 µV, and 32.5 µV, respectively. The threshold values are indicated by dot-dash lines in FIGS. 6(a) to (c).

FIGS. 6(a) to (c) and the table in FIG. 6 indicate that, as in the probability distribution for region 1 (central visual region) of FIG. 6(a) and the probability distribution for region 2 of FIG. 6(b), there is a considerable overlap between the probability distribution of the case where the amount of attention is large and the probability distribution of the case where the amount of attention is small. It can also be seen that the values of the attention amount distinction rates are as low as 55.4% and 59.8%, respectively.

On the other hand, in region 3 (peripheral visual field) with a viewing angle of 20° or more of FIG. 6(c), there is a certain degree of separation between the probability distribution of the case where the amount of attention is large and the probability distribution of the case where the amount of attention is small, and the attention amount distinction rate is 73.7%, which is a quite high value for a determination using a non-cumulative electroencephalogram.

This leads to the finding that, by determining the amount of attention by utilizing the P300 of an event-related potential with respect to a stimulation occurring in the peripheral visual region, a high distinction rate can be constantly obtained with a non-cumulative electroencephalogram, without having to perform a summation on the order of tens to hundreds of times.

However, in the case where an amount of attention is to be determined based on the finding obtained above, the threshold used for the attention amount determination greatly differs from individual to individual, and an accurate determination cannot be made if the attention amount determination is made by using as a threshold a standardized numerical value which is common to all, e.g., an average value.

This will be described in more detail below.

Figure 7:
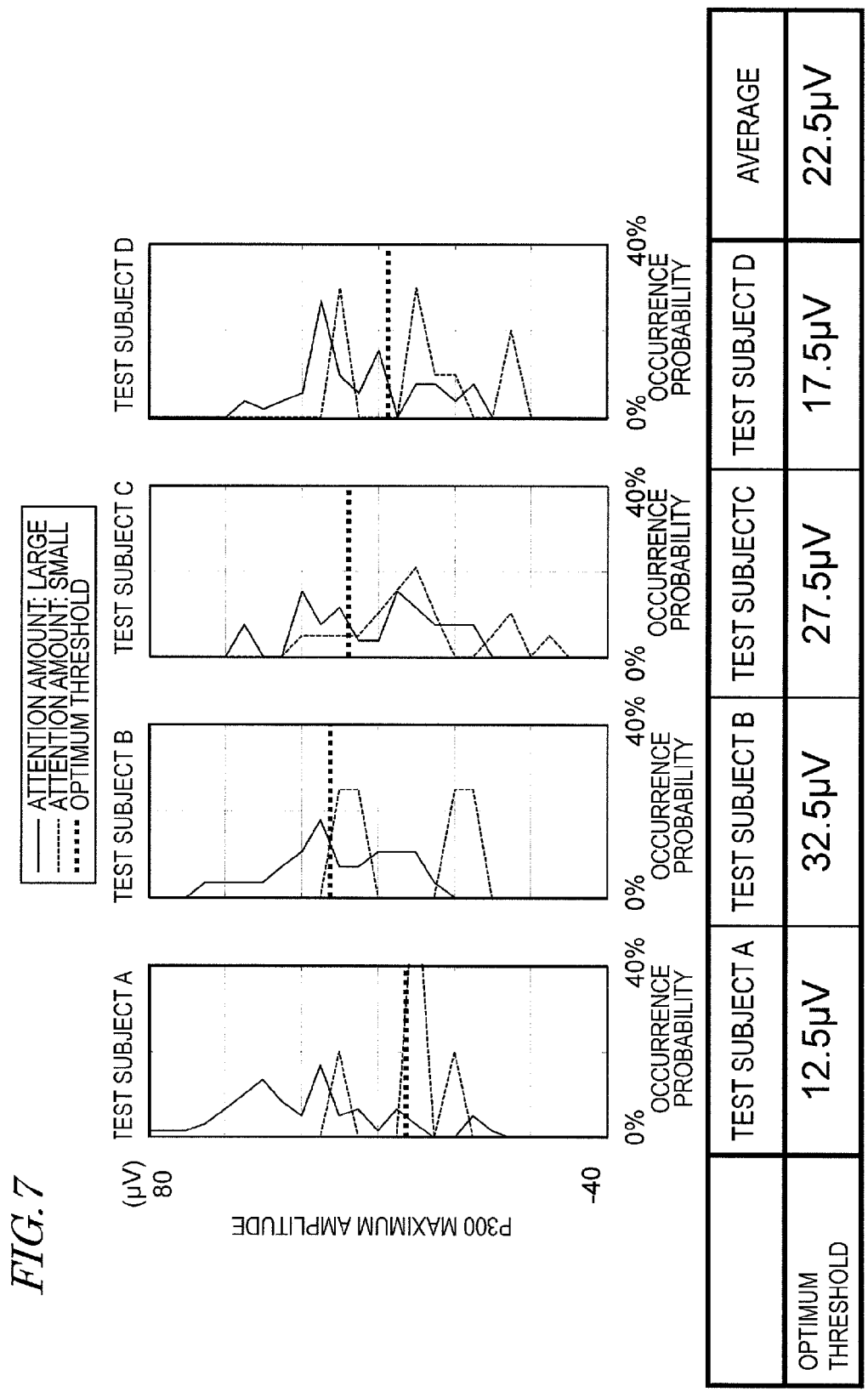
FIG. 7 is a diagram showing P300 maximum amplitude probability distributions of a non-cumulative electroencephalogram and thresholds that maximize the distinction rate with respect to different test subjects.

FIG. 7 shows, with respect to each test subject, a P300 maximum amplitude probability distribution of a non-cumulative electroencephalogram and a threshold that maximizes the distinction rate. This threshold defines the maximum distinction rate for each test subject, and thus can be regarded as the optimum threshold for that test subject. Therefore, the threshold that maximizes the distinction rate will hereinafter be referred to as the "optimum threshold".

In each graph in FIG. 7, the vertical axis represents potential in units of µV, and the horizontal axis represents occurrence probability for the respective amounts of attention in units of %. A lateral dotted line in each graph represents an optimum threshold for attention amount determination. The table under the graph shows the value of the optimum threshold of each test subject. For four test subjects A to D, the optimum thresholds were 12.5 µV, 32.5 µV, 27.5 µV, and 17.5 µV. Thus, individual variations exist among the optimum threshold values. The distinction rate obtained by performing an attention amount determination by utilizing the optimum threshold of each individual above was 73.7% on average. On the other hand, a distinction rate of 66.1% was obtained by, without considering differences in threshold between individuals, performing an attention amount determination by using an average optimum threshold value of 22.5 µV as a threshold. This is a lower distinction rate than that obtained by taking the threshold of each individual into consideration. Therefore, in order to maintain a sufficient accuracy of determination, it is necessary to consider individual differences in setting a threshold.

One method of determining an optimum threshold for each individual might be to ask the individual to drive in a state of focused attention or distraction in advance, and previously measure electroencephalograms in such states to determine an optimum threshold. However, previously performing a trial for such calibration will be a burden on the driver. Moreover, it would be unrealistic to drive in a state of distraction.

Accordingly, the inventors have analyzed the aforementioned experiment by paying attention to the P300 distribution in the central visual field as a value that is related to the optimum threshold of each individual. Thus, we have arrived at the finding that, even without distinguishing the amount of attention to be large or small, the optimum threshold is correlated to the median of a P300 distribution of an event-related potential with respect to stimulations occurring in the central visual region. As used herein, a median represents a value which lies in the center when data are placed in a size-based order. Hereinafter, the case of utilizing a median rather than an average value, due to reduced influence of outliers as is set forth in previous literature (Tsuyoshi YAMADA et al., YOKUWAKARU SHINRITOUKEI (or "Psychological Statistics Made Easy"), 2004, p30-33, Minerva Shobo), will be described as an example.

Hereinafter, the aforementioned novel findings will be described, followed by a description of an embodiment where an attention amount determination is performed by setting an attention-amount determination threshold for each individual without performing any previous calibration.

In order to set a threshold without previously acquiring electroencephalogram data of driving in a state of focused attention or distraction, it is necessary to set a threshold by utilizing an electroencephalogram after a driver has commenced driving. Based on two characteristic features obtained from FIG. 5, the inventors paid attention to the P300 distribution in the central visual region as a parameter that is correlated to the optimum threshold.

A first characteristic feature is that the center of distribution (an intermediate between a large attention amount and a small attention amount) of P300 in region 1 (central visual region) and the center of distribution (an intermediate between a large attention amount and a small attention amount) of P300 in region 3 (peripheral visual region) (hereinafter, peripheral stimulation-P300) have relatively close values. This is also true of the relationship between the center of distribution of P300 in region 2 and the center of distribution of peripheral stimulation-P300 in region 3. With respect to each individual, too, it is considered that the center of distribution of P300 in the central visual region and the center of distribution of P300 in the peripheral visual region are closely related, and it is expected that there is a correlation between the P300 distribution in the central visual region and the optimum threshold, assuming that the center of distribution of P300 in the peripheral visual region is the optimum threshold.

A second characteristic feature is that: in region 3 (peripheral visual region), there is a large difference in P300 distribution between a state of large attention amount and a state of small attention amount; however, in region 1 (central visual region), the distributions of a state of large attention amount and a state of small attention amount are huddled close together. When setting a threshold by utilizing an electroencephalogram during driving, this makes it impossible to distinguish whether an acquired electroencephalogram pertains to a state of focused driving or a state of distraction.

These characteristic features indicate the following. Unlike in an experimental situation where the driving state is under control, in an actual driving situation, there is no given distinction as to a state of focused driving or a state of distraction. Therefore, a distribution which is obtained in a driving situation may strongly reflect a focused state, or strongly reflect a state of distraction; in this case, too, it is necessary to determine a determination threshold which supports individual differences. From this standpoint, the characteristics that the average amplitude values of when focused and when distracted are close in the central visual region are difficult to be used as a piece of information for determination, but is considered effective as an index (determination threshold) indicating a fundamental amplitude of that driver. An individual difference can be expressed as a difference in the baseline of amplitude, and the distribution in the central visual field can be considered as expressing a fundamental amplitude of the driver, regardless of the state of attention in driving. When taken together with the first finding in the aforementioned characteristic features, it would follow that this amplitude which is determined from the central visual field is also effective as a threshold with which to determine a state of attention in the peripheral visual field.

Therefore, when calculating the center of distribution of P300 with respect to visual stimulations which are presented in the peripheral visual region (hereinafter referred to as "peripheral stimulations"), the calculated center will be biased depending on whether the driver is in a state of focused driving or a state of distraction. For example, if the driver is in a distracted state, if a center is calculated by using the peripheral stimulation-P300 distribution, the center of distribution will have a small value than the optimum threshold. However, P300 of visual stimulations which are presented in the central visual region (hereinafter referred to as "central stimulations") is such that the P300 amplitude is almost similarly distributed in a state of focused driving and in a state of distraction, and thus the center of distribution of P300 is hardly affected regardless of the state of attention of the driver. Therefore, when setting a threshold in a state where the amount of attention of a driver is unknown, it is considered effective to utilize the central stimulation-P300 distribution.

In accordance with the above characteristic features, as a method of calculating the center of distribution, a median, which is not susceptible to much outlier influence, was utilized; and the correlation between the median and optimum threshold of the central stimulation-P300 distribution was analyzed.

Figure 8:
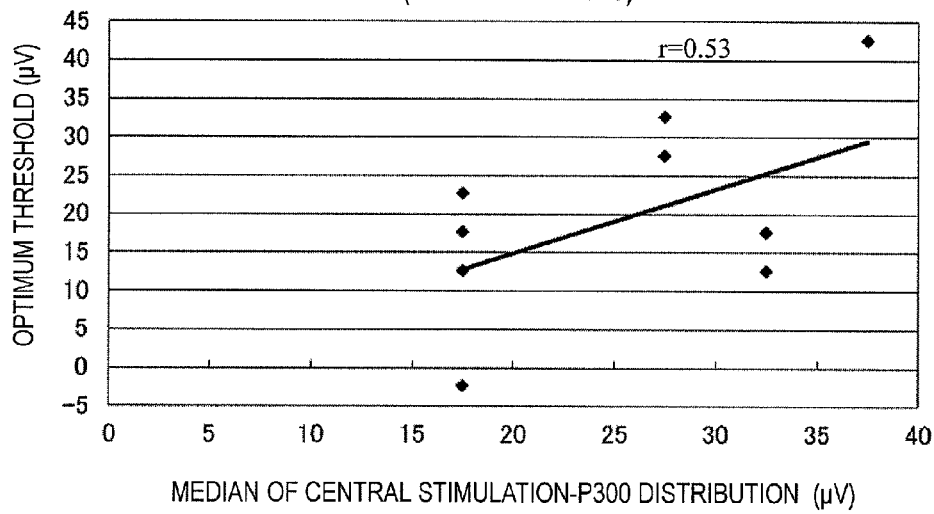
FIG. 8 is a graph of medians and optimum thresholds, of a P300 distribution of an event-related potential with respect to stimulations occurring in the central visual region (central stimulation P300 distribution), in 10 test subjects.

FIG. 8 shows a graph of medians and optimum thresholds, of a P300 distribution of an event-related potential with respect to stimulations occurring in the central visual region (central stimulation P300 distribution), in 10 test subjects. In the graph, the horizontal axis represents the median of the central stimulation P300 distribution in units of μV, and the vertical axis represents the optimum threshold in units of μV. Each test subject is represented by a single plot, and a solid line indicates an approximate line for all of the plots. There seems some variation in the optimum threshold and the median of the central stimulation P300 distribution among the respective individuals. A correlation coefficient r between the optimum threshold and the median of the central stimulation P300 distribution of all test subjects was calculated to be r=0.53. Generally speaking, according to previous literature (Tsuyoshi YAMADA et al., YOKUWAKARU SHINRI-TOUKEI (or "Psychological Statistics Made Easy"), 2004, p55, Minerva Shobo), a correlation coefficient of 0.4 or more can be regarded as indicating a moderate correlation. Therefore, since the correlation coefficient exceeds 0.5, it can be determined that there is moderate correlation between the optimum threshold and the median of the central stimulation P300 distribution.

The above results have led to the finding that there is correlation between the median of P300 in the central visual field and the optimum threshold, such that an optimum threshold can be calculated by using a median of P300 in the central visual field.

By utilizing the above finding, a driving attention determination apparatus can be realized which, by measuring a central stimulation-P300 distribution and setting a threshold by using the center of distribution (e.g., a median), performs a determination adapted to each individual, without previously acquiring electroencephalogram data of driving in a state of focused attention or distraction.

Hereinafter, embodiments of the present invention based on this concept will be described with reference to the figures.

Embodiment 1

Figure 9:
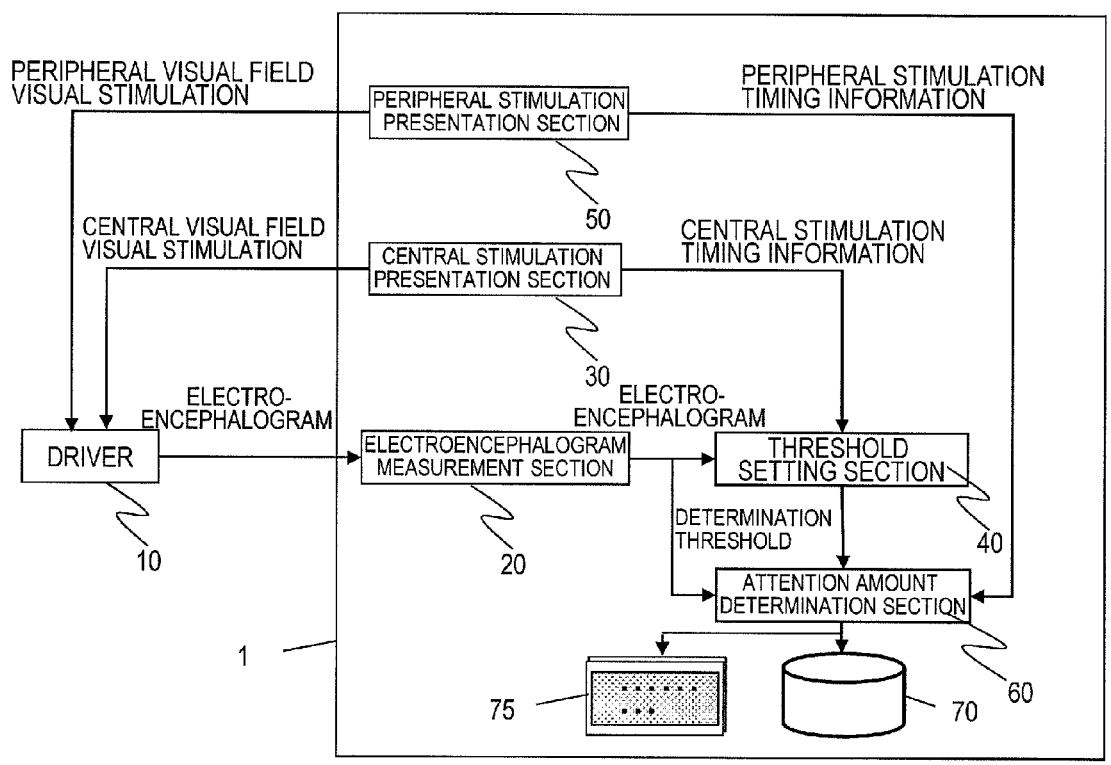
FIG. 9 is a diagram showing a block construction of a driving attention amount determination apparatus 1 according to Embodiment 1.

FIG. 9 shows the block construction of a driving attention amount determination apparatus 1 according to the present embodiment.

The driving attention amount determination apparatus 1 is an apparatus for determining a driver's 10 amount of attention to driving by utilizing an electroencephalogram signal from the driver 10, and providing assistance in accordance with the result of determination.

The driving attention amount determination apparatus 1 includes an electroencephalogram measurement section 20, a central stimulation presentation section 30, a threshold setting section 40, a peripheral stimulation presentation section 50, an attention amount determination section 60, a storage section 70, and a display panel 75. The driver 10 block is illustrated for ease of description.

The electroencephalogram measurement section 20 measures an electroencephalogram of the driver 10.

The central stimulation presentation section 30 generates a visual stimulation in the central visual region of the driver 10. In the present specification, visual stimulations which are presented in the central visual region are referred to as "central stimulations".

From the electroencephalogram signal measured based on the time point of occurrence of a central stimulation as a starting point, and the threshold setting section 40 sets a threshold for use in the attention amount determination.

The peripheral stimulation presentation section 50 generates a visual stimulation in the peripheral visual region of the driver 10. In the present specification, visual stimulations which are presented in the peripheral visual region are referred to as "peripheral stimulations".

The attention amount determination section 60 determines an amount of attention of the driver 10 to the peripheral visual region, from an electroencephalogram signal which is measured based on the time point of occurrence of the peripheral stimulation as a starting point and from the aforementioned threshold.

The storage section 70 is a storage device for storing the data of results of determination in a storage medium. As the storage medium, a silicon disk (semiconductor storage medium) such as a USB-connectable or memory card-type flash memory or an SSD, a magnetic storage medium such as a hard disk drive, and an optical disk medium such as a DVD or BD are contemplated.

The display panel 75 is a display device for displaying a result of determination. For example, the display panel 75 is a liquid crystal panel which is provided in the driving attention amount determination apparatus 1.

Hereinafter, the respective constituent elements will be described in detail.

The electroencephalogram measurement section 20 is an electroencephalograph for measuring an electroencephalogram signal, i.e., changes in the potentials at electrodes which are worn on the head of the driver 10. The inventors envisage that a wearable-type electroencephalograph will be used in future. Therefore, the electroencephalograph may be a head-mount type electroencephalograph. It is assumed that the driver 10 has worn the electroencephalograph in advance.

Electrodes are disposed on the electroencephalogram measurement section 20 so that, when worn on the head of the driver 10, the electrodes come in contact with the head at predetermined positions. The positions of the electrodes may be, for example, Pz (median parietal), A1 (earlobe), and the nasion. According to previous literature (Yo MIYATA et al., "New Physiopsychology", 1998, p. 119, Kitaoji Shobo), P300, which is a positive component that reflects perception of or attention to an external stimulation and appears near about 300 milliseconds based on the timing of occurrence of the stimulation as a starting point, is supposed to rise to its maximum amplitude at Pz (median parietal). However, P300 measurement is also possible at Cz (epicranium) or Oz (occiput), which are in the neighborhood of Pz, and therefore electrodes may be disposed in these positions. These electrode positions are to be determined based on reliability of signal measurements, wearing ease, and the like.

The central stimulation presentation section 30 and the peripheral stimulation presentation section 50 present stimulations in the central visual region and the peripheral visual region of the driver 10, respectively. These may be projectors, LEDs, and displays (including control circuitry for light activation), for example. The method of stimulation presentation may be by projection onto the windshield of an automobile, for example. Alternatively, under the assumption that the driving attention amount determination apparatus 1 is a glasses-type head-mount display (Head Mounted Display (HMD)), it is also possible to present stimulations on the display of the HMD. Furthermore, in the case where the driving attention amount determination apparatus 1 is incorporated into a driving simulator (Driving Simulator (DS)), it is also possible to present stimulations on the screen of the DS. Each such specific implementation will be later described in detail with reference to FIGS. 11, 21, and 22.

Note that the central visual region 151 and the peripheral visual region 152 may change. For example, the field of vision of a driver may change depending on brightness, the traveling velocity of the car, and the like. Therefore, in the case where the velocity of the driver's vehicle has increased, the positions at which the central stimulation presentation section 30 and the peripheral stimulation presentation section 50 present stimulations may be changed through adjustments on the assumption that the central visual region 151 has become smaller than what is usually set and that the peripheral visual region has increased.

For instance, an exemplary case will be described, under the assumption that the area of the central visual region has a 40% decrease at 100 km per hour as compared to at 50 km per hour. When traveling at 50 km per hour or less, e.g., in town, the central stimulation presentation section 30 presents a visual stimulation by setting the central visual region to be a region spanning 20 degrees in up and down directions and right and left directions from a fixation point 150, as shown in FIG. 4. On the other hand, when traveling at a velocity above 100 km per hour, e.g., on an expressway, the central visual field will be a region spanning 15 degrees in up and down directions and right and left directions, which is reduced by 40% from the area of the central visual region. Therefore, the central stimulation presentation section 30 sets the central visual region to be a region spanning 15 degrees in up and down directions and right and left directions from the fixation point, and presents a visual stimulation in this range. On the other hand, the peripheral stimulation presentation section 50 sets the region outside this to be the peripheral visual region, and presents a visual stimulation in this range.

Instead of defining the central visual region in terms of a viewing angle range from a fixation point as in the above, a range within the same lane in the front of the driver's vehicle may be set as a region which can be clearly grasped.

By using a characteristic signal with respect to a stimulation which is presented by the central stimulation presentation section 30, the threshold setting section 40 sets a threshold for determining an amount of attention. Although described with respect to P300 above, signals with close latency ranges, e.g., N200, P200, P600, are also considered to appear with similar tendencies as a characteristic signal of an event-related potential. Hereinafter, among the aforementioned characteristic signal, P300 will be discussed as a characteristic signal. Note that N200 is a negative component of no less than 150 milli- to no more than 250 milliseconds. P200 is a positive component of no less than 150 milli- to no more than 250 milliseconds. P600 is a positive component of no less than 400 milli- to no more than 800 milliseconds.

By utilizing a characteristic signal of an electroencephalogram with respect to a stimulation which is presented by the peripheral stimulation presentation section 50, the attention amount determination section 60 determines an amount of attention of the driver 10. Although described with respect to P300 above, signals with close latency ranges, e.g., N200, P200, P600, are also considered to appear with similar tendencies as a characteristic signal. Hereinafter, among the aforementioned characteristic signal, P300 will be discussed as a characteristic signal. Note that the characteristic signal which is utilized by the attention amount determination section 60 is the same characteristic signal as that utilized by the threshold setting section 40.

The result of attention amount determination may be stored to the storage section 70, or recorded and stored in a recording device (HDD or the like) which the attention amount determination section 60 possesses. Moreover, the result of determination may be fed back to the driver 10 by using the display panel 75. In the case where the attention amount determination section 60 possesses an output device such as a display, that output device may be utilized.

The present embodiment will be described with respect to an example where the driving attention amount determination apparatus 1 is incorporated into a driving simulator (DS) at a driving school.

Figure 10:
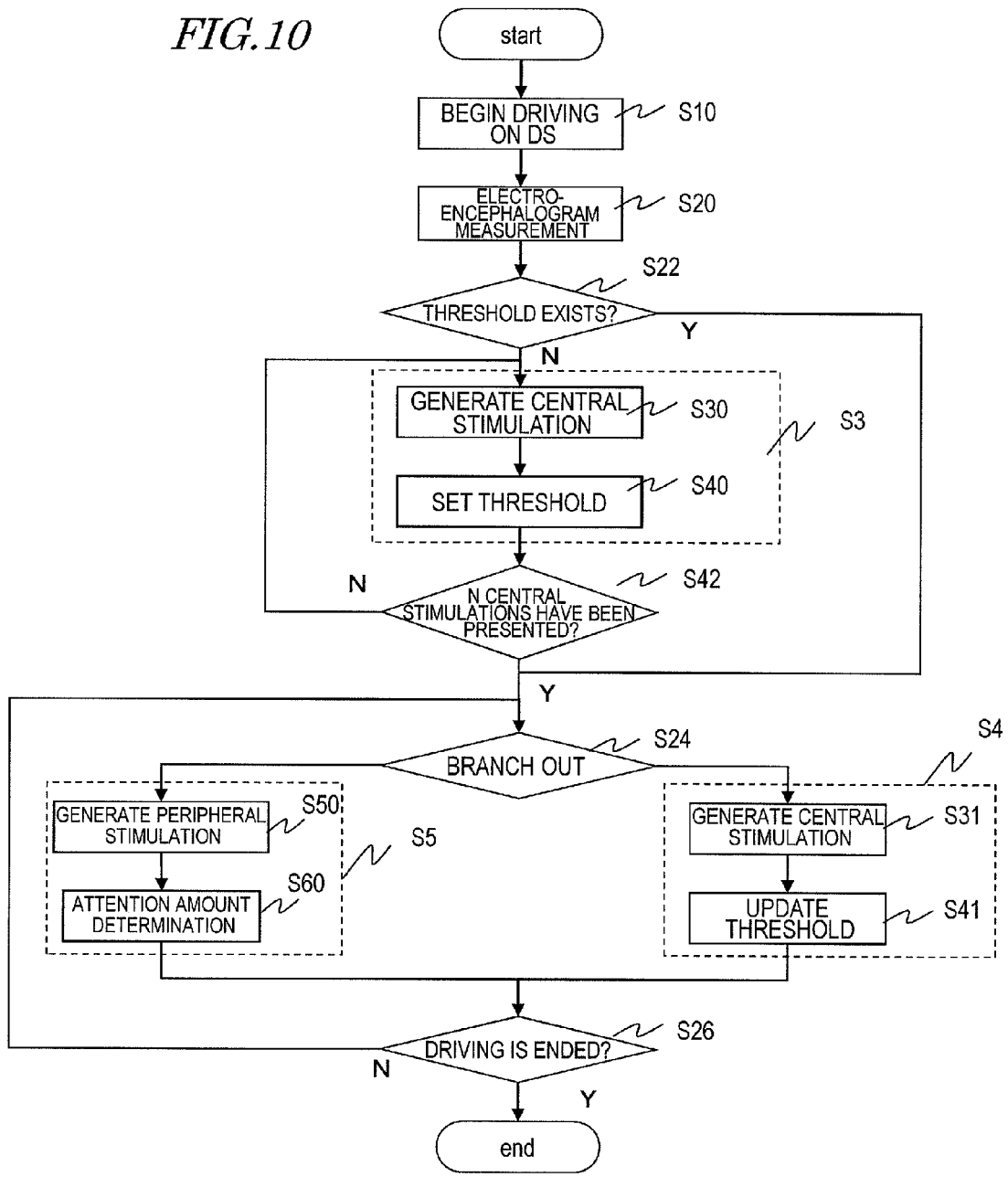
FIG. 10 is a flowchart of an overall processing by the driving attention amount determination apparatus 1.

FIG. 10 shows a flowchart of the overall processing of the driving attention amount determination apparatus 1. Hereinafter, an operation will be described with reference to the flowchart of the driving attention amount determination apparatus 1 in FIG. 10.

At step S10, the driver 10 begins driving on the DS. Once the driving on the DS is begun, the process of attention amount determination by the driving attention amount determination apparatus 1 is also begun, and as for the brain, electroencephalogram measurement by the measurement section 20 is begun.

At step S20, the electroencephalogram measurement section 20 measures an electroencephalogram of the driver 10. The measured electroencephalogram is sampled so as to be computer-processable, and is sent to the threshold setting section 40 and the attention amount determination section 60. Note that, in order to reduce the influence of noises mixing into the electroencephalogram, the electroencephalogram measured by the electroencephalogram measurement section 20 is previously subjected to a 15 Hz low-pass filtering process, for example.

At step S22, the threshold setting section 40 confirms whether a threshold for attention amount determination is set in the attention amount determination section 60 or not. If no threshold is set, control proceeds to step S3 to set a threshold. If a threshold is already set, the process proceeds to a step S24 to branch between step S4 of enhancing the threshold accuracy and step S5 of determining the amount of attention.

Step S3 of setting a threshold consists of step S30 of generating a central stimulation and step S40 of setting a threshold.

At step S30, the central stimulation presentation section 30 presents a visual stimulation in the central visual region of the driver 10.

Figure 11A:
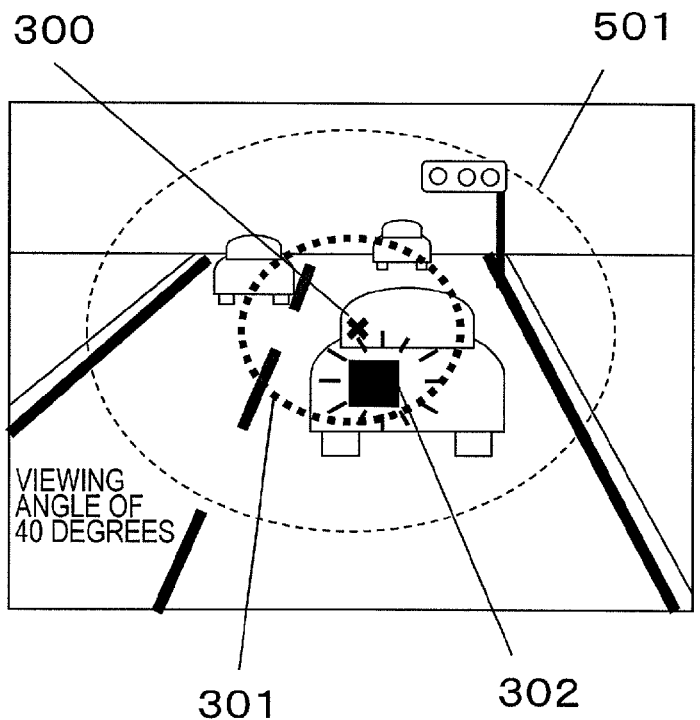
FIGS. 11A and 11B are diagrams showing examples of stimulation presentation.
Figure 11B:
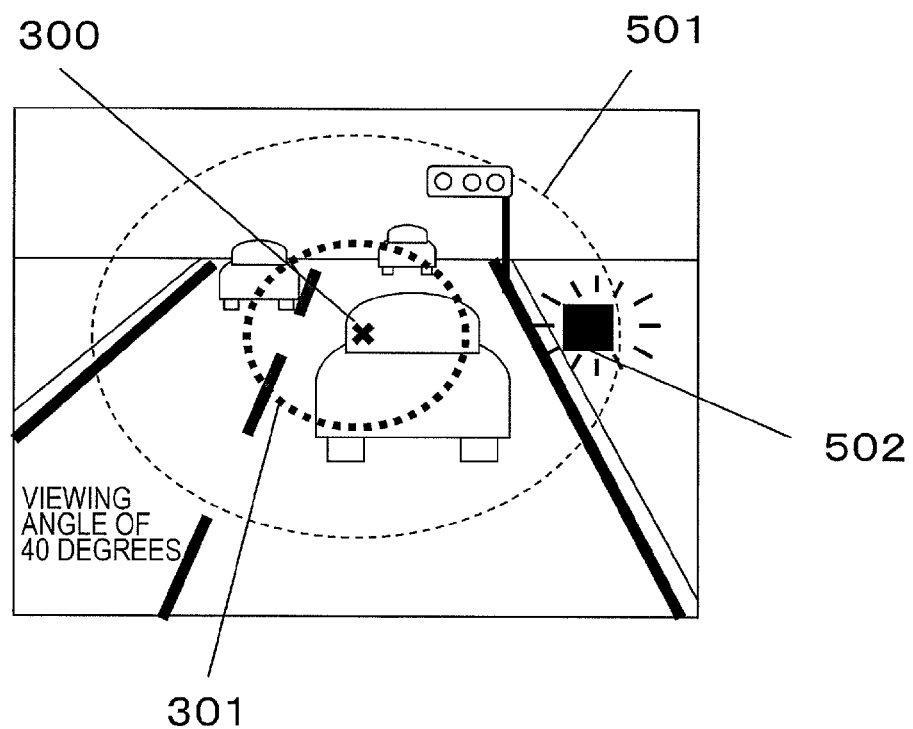

An example of stimulation presentation is shown in each of FIGS. 11A and 11B. FIG. 11A shows an example of an image which is indicated on a display that is in the front direction of the DS. A fixation point 300 of the driver is indicated by an x symbol, and a range spanning a viewing angle of 20 degrees from the fixation point 300 (a range totaling 40 degrees) defines a central visual region 301. A central visual field visual stimulation 302 is presented at an arbitrary position in the central visual region 301. (The x symbol of the fixation point 300 and a dotted line of the visual region are illustrated for the sake of explanation, and are not displayed on the screen). In the case where the central visual field visual stimulation 302 is presented by using an LED, the LED may be provided as a point light source.

The central stimulation presentation section 30 sends information indicating the timing of presenting the stimulation to the threshold setting section 40.

FIG. 10 is again referred to.

At step S40, the threshold setting section 40 cuts out an event-related potential based on the measured electroencephalogram and the information indicating the timing of presenting the stimulation in the central visual region, and extracts P300.

The threshold setting section 40 retains the P300 amplitude distribution of the event-related potential, and sets a threshold by calculating a median of the distribution. The details of the process will be described later.

The threshold setting section 40 sets a threshold based on the median of the central stimulation-P300 distribution. However, when there is not much data of measured P300, the threshold setting section 40 is unable to analyze the P300 distribution, and thus unable to calculate a median. Therefore, at step S42, the threshold setting section 40 confirms whether or not an enough number of central stimulation-P300's are stored for calculating a median of the distribution. Herein, the threshold setting section 40 confirms whether presentation of a central stimulation has been made N times (e.g. 5 times) or not; if presentation has been made N or more times, it determines that a median has been appropriately calculated and proceeds to branching process of step S24. If presentation has not been made N or more times, it determines that the number of data of central stimulation-P300 is insufficient and that a median has not been appropriately calculated, and returns to the process of step S30 to present a central stimulation. As will be mentioned later, N is an integer of 5 or more in the present embodiment.

When there is a threshold that has been set, step S24 branches out to step S4 of enhancing the threshold accuracy or step S5 of determining the amount of attention. Through this branching, it is determined whether to again set a threshold or determine the amount of attention, as the next stimulation-presenting process. In order not to allow the driver to predict the timing of attention determination, the process of step S4 and the process of step S5 are randomly switched. Note that any method of switching between the processes according to a predetermined order, e.g., alternately performing the processes of step S4 and step S5, may also be safely used.

Similarly to step S3 of setting a threshold, the process S4 of enhancing the threshold accuracy consists of step S30 of generating a central stimulation and step S40 of setting a threshold.

At step S31, the central stimulation presentation section 30 presents a visual stimulation in the central visual region of the driver 10. The method of stimulation presentation is similar to the presentation of a central stimulation at step S30. After the stimulation presentation, the central stimulation presentation section 30 sends information indicating the timing of presenting the stimulation to the threshold setting section 40.

At step S41, the threshold setting section 40 performs a process of updating the threshold for attention amount determination. The threshold setting section 40 extracts the P300 amplitude from the measured event-related potential with respect to the central stimulation, and adds the P300 data to the P300 distribution generated at step S40. Since the data amount of P300 with respect to central stimulations is increased, the accuracy of the P300 distribution can be enhanced. The threshold setting section 40 again calculates a threshold by calculating a median of the P300 distribution. Since the accuracy of the P300 distribution is enhanced, the accuracy of the calculated median and threshold is also enhanced.

It is considered that the P300 distribution of each person does not change so long as the driving time is in the range of several minutes to 2 or 3 hours. However, in a time range of several days or several weeks, it is considered that the P300 distribution will change within the same individual. Therefore, as for the range of central stimulation-P300 data to be used for threshold setting, it is desirable to regard the same driving (after starting the engine and until stopping the engine) as one unit for analysis, and set one threshold.

By increasing the number of times of central stimulation presentation at step S4, the population parameter of the P300 amplitude distribution of the event-related potential is increased in the process of the threshold setting section 40 at step S40, whereby the accuracy of the median of the distribution can be improved. Since the accuracy of the median of the distribution is improved, the accuracy of the threshold adapted to each individual can be improved.

Step S5 of determining the attention amount consists of step S50 of generating a peripheral stimulation and step S60 of determining the attention amount.

At step S50, the peripheral stimulation presentation section 50 presents a visual stimulation in the peripheral visual region of the driver 10. A position at which a stimulation in the peripheral visual field is to be displayed will be described in FIG. 11B. A peripheral visual region 501 is a region spanning 130 degrees in up and down directions and 180 degrees in right and left directions from a fixation point 300, excluding the central visual region. Therefore, a visual stimulation is to be displayed at an arbitrary position outside the central visual region 301 and inside the peripheral visual region 501.

An example of peripheral stimulation presentation is shown in FIG. 11B. Similarly to FIG. 11A, FIG. 11B shows an example of an image which is indicated on a display that is in the front direction of the DS. A fixation point 300 of the driver is indicated by an x symbol, and a range spanning 130 degrees in up and down directions and 180 degrees in right and left directions from a fixation point 300, excluding the central visual field, is a peripheral visual region 501. A peripheral visual field visual stimulation 502 is presented at an arbitrary position in the peripheral visual region 501. (The x symbol of the fixation point 300 and a dotted line of the visual region are illustrated for the sake of explanation, and do not need to be displayed on the screen). The peripheral stimulation presentation section 50 sends information indicating the timing of presenting the stimulation to the attention amount determination section 60.

At step S60, based on the measured electroencephalogram and the information indicating the timing of presenting the stimulation in the peripheral visual region, the attention amount determination section 60 cuts out an event-related potential, and extracts a characteristic signal. The attention amount determination section 60 compares the P300 amplitude of the event-related potential against the threshold.

If the P300 amplitude falls below the threshold (i.e., the amplitude value of P300 is smaller than the threshold), the attention amount determination section 60 determines a state of distraction. On the other hand, if the amplitude rises above the threshold (i.e., the amplitude value of P300 is equal to or greater than the threshold), the attention amount determination section 60 determines a state of focused driving. The attention amount determination section 60 stores the result of determination to the storage section 70. The details of the process will be described later.

After step S4 of enhancing the threshold accuracy or step S5 of determining the amount of attention is performed, a confirmation is made at step S26 as to whether the driver 10 is still driving or not. The criterion for determining whether or not driving is being continued may be as follows. For example, in an environment where a DS is used, a determination that driving is being continued may be made until a complete round of a predetermined course of interest has been made. In the case of an actual car, a determination that driving is being continued may be made until the engine is turned off.

In the case where driving is being continued, determination of the driving attention amount is also continued, and control proceeds again to the branching process of step S24, whereby either a threshold setting or a process of attention amount determination is performed. When driving is ended, the processing by the driving attention amount determination apparatus 1 is also ended.

Figure 12:
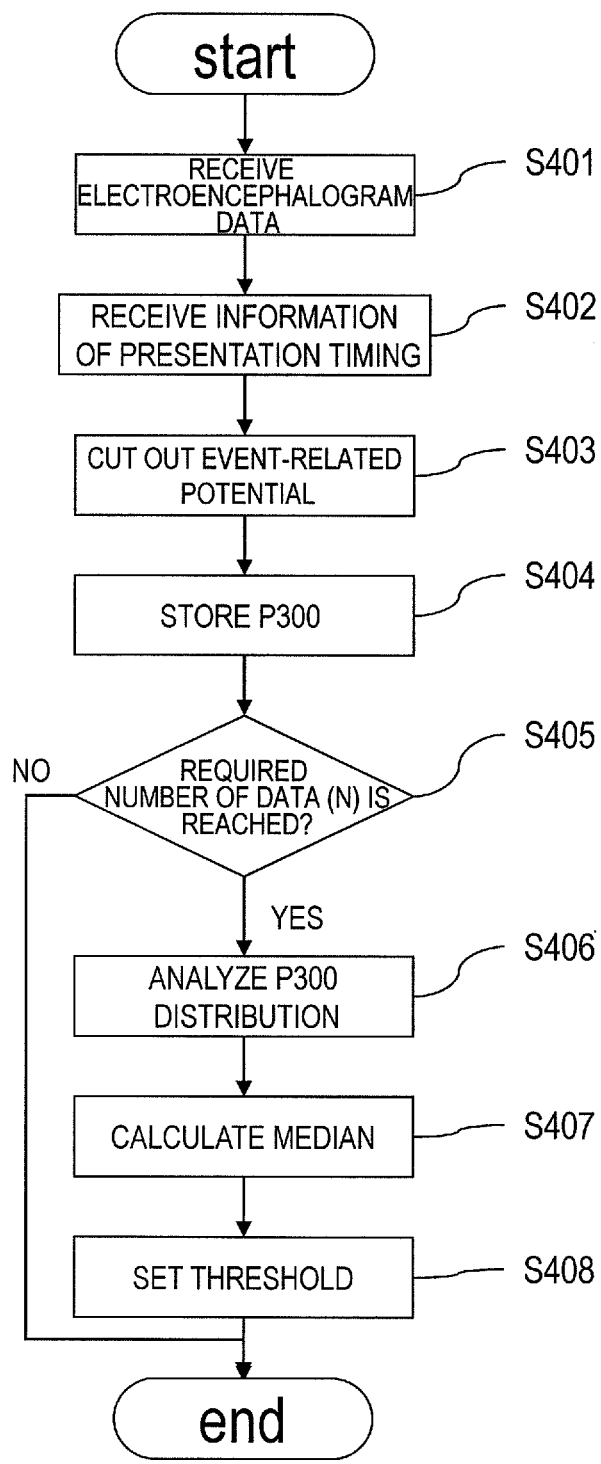
FIG. 12 is a flowchart showing flow of processes at step S40 (FIG. 10) which is conducted by a threshold setting section 40.

Next, the details of the process of threshold setting performed at step S40 will be described. FIG. 12 is a flowchart showing a flow of processes of step S40 that are performed by the threshold setting section 40. The threshold setting is performed by utilizing stimulations which are presented in the central visual field. Through the following processes, a threshold adapted to each individual can be set without previously acquiring electroencephalogram data of driving in a state of focused attention or distraction.

At step S401, the threshold setting section 40 receives an electroencephalogram which is measured by the electroencephalogram measurement section 20. An example of a measured electroencephalogram is shown in FIG. 13(a). In the graph, the horizontal axis represents time, and the vertical axis represents electroencephalogram potential.

At step S402, from the central stimulation presentation section 30, the threshold setting section 40 receives information indicating the timing of presenting the stimulation in the central visual field. Examples of timing of presenting central stimulations are shown in FIG. 13(b). The horizontal axis represents time, and the positions of black triangles indicate the timing of presenting central stimulations.

At step S403, the threshold setting section 40 extracts an electroencephalogram based on the timing of presenting the central stimulation as a starting point. Specifically, based on the timing of presenting the stimulation in the central visual region as a starting point (0 ms), electroencephalogram data from −100 milliseconds to 600 milliseconds is cut out. FIG. 13(c) shows an example of electroencephalogram data having been cut out. In the graph, the horizontal axis reproduces time (milliseconds), and the vertical axis represents potential (μV). The threshold setting section 40 subjects the electroencephalogram having been cut out to a baseline correction with respect to an average potential from −100 milliseconds to 0 milliseconds, based on the point in time of generating the stimulation as a starting point.

At step S404, the threshold setting section 40 stores a P300 amplitude value of the event-related potential contained in the electroencephalogram data having been cut out. P300 is measured in terms of the amplitude value of a positive peak (local maximum) appearing near about 300 milliseconds. FIG. 13(c) shows an example of P300 amplitude 101. The size of the amplitude 101 is stored as the P300 amplitude. In the case of FIG. 13(c), the P300 amplitude is 10.0 μV.

At step S405, the threshold setting section 40 checks the number of stored P300 data. For one presentation of a central stimulation, a single P300 is stored. In order to analyze the P300 distribution, a plurality of P300 data are required. Herein, a confirmation is made as to whether the number of stored P300's has reached the required data (N) or not. For example, assuming that five is the smallest number for distribution reliability, then N=5, and it is checked whether the number of stored P300's has exceeded five or not. If the required number of data is exceeded, control proceeds to step S406, and the process of threshold setting is continued. If the required number of data is not reached, the process is finished without performing threshold setting.

At step S406, the threshold setting section 40 analyzes the distribution of stored P300's. The P300 amplitude values and their occurrence frequencies are checked, and the P300 distribution with respect to central stimulations is analyzed. An exemplary P300 distribution analyzed in the above experiment is shown in FIG. 14. FIG. 14 shows an exemplary P300 amplitude distribution with respect to 216 central stimulations. In the graph of FIG. 14, the vertical axis represents the potential of P300 amplitude (μV), and the horizontal axis represents the occurrence frequency at each potential. The P300 distribution is done without making a distinction between a state of focused driving or a state of distraction of the driver 10.

At step S407, based on the analyzed P300 distribution, the threshold setting section 40 calculates a median of P300 amplitudes with respect to central stimulations. By utilizing the median, a center of distribution can be calculated in which the influences of outliers such as accidentally-mixed body motion noises are reduced. In the example of FIG. 14, the amplitude value of 21.0 μV, at which the center of occurrence frequencies is located, is the median.

At step S408, the threshold setting section 40 sets a threshold for attention amount determination. Herein, based on the finding (FIG. 8) that there is a correlation between the median of the central stimulation-P300 distribution and the optimum threshold, the median calculated at step S407 is adopted as the threshold for attention amount determination, and this threshold is set in the attention amount determination section 60. In other words, 21.0 μV is set as a threshold for attention amount determination.

In the above procedure, by utilizing the median of the P300 distribution for stimulations in the central visual field, a threshold for attention amount determination that is adapted to each individual can be set.

Although a median is utilized for reducing outlier influences at step S407 in the above example, any other method for determining a center of distribution method (e.g., an average value) can be used so long as a center can be determined.

Next, the details of the attention amount determination process performed at step S60 will be described. FIG. 15 is a flowchart showing a flow of processes of step S60 that are performed by the attention amount determination section 60. The attention amount determination is performed by utilizing stimulations that are presented in the peripheral visual field.

At step S601, the attention amount determination section 60 receives an electroencephalogram which is measured by the electroencephalogram measurement section 20.

At step S602, the attention amount determination section 60 receives information indicating the timing of presenting the stimulation in the peripheral visual field by the peripheral stimulation presentation section 50.

At step S603, the attention amount determination section 60 extracts electroencephalogram data based on the timing of presenting the peripheral stimulation as a starting point. Similarly to step S403 performed by the threshold setting section 40, the attention amount determination section 60 cut outs electroencephalogram data from 100 milliseconds to 600 milliseconds based on the timing of presenting the stimulation as a starting point (0 ms), and performs a baseline correction with respect to an average potential from −100 milliseconds to 0 milliseconds.

At step S604, the attention amount determination section 60 stores data of event-related potential waveforms contained in the electroencephalogram data. The storage utilizes a storing means (e.g., memory) which is accessible to the attention amount determination section 60. The memory may be a common memory that is accessed by functional blocks other than the attention amount determination section 60.

At step S605, the attention amount determination section 60 determines whether the number of electroencephalogram data stored at step S604 has reached a required number of summations that is set in advance. If the number is not reached, the process of attention amount determination is finished; if it is reached, control proceeds to S606.

In connection with the next step S606, a method of attention amount determination according to the present embodiment will be described.

In the studies of event-related potentials in general, an analysis is performed after deriving an arithmetic mean of electroencephalogram data. As a result, action potentials of the brain that are not in synchronization with the encephalic activity at issue, called the background electroencephalogram, are counteracted, thus making it possible to detect an event-related potential (e.g. P300) that has a certain latency (i.e., amount of time in which an action potential occurs based on the time point of occurrence of a stimulation as a starting point) and polarity. For example, in a piece of previous literature (Yo MIYATA et al., "New Physiopsychology", 1998, p. 110, Kitaoji Shobo), 30 rounds of arithmetic mean processes are performed.

Therefore, in the present embodiment, too, it is assumed that an arithmetic mean calculation is conducted to perform an analysis process for attention amount determination.

As the method of summation, a time sliding approach may be adopted, for example. FIG. 16 shows arithmetic mean waveforms 1 to 5 that are obtained by adopting a time sliding approach. This example is an approach where waveforms from a designated number of times (e.g. 5 times) are summed up, such that, when a new waveform is input, the oldest waveform is excluded and an arithmetic mean is taken of the waveforms from the designated number of times, thus generating an arithmetic mean waveform. This approach makes it possible to generate a summed waveform which quickly follows changes in waveform over time.

Moreover, a summed waveform to be output per predetermined time period can also be generated. A technique of calculating a summed waveform per time period is an effective method in an actual environment where stimulations cannot be controlled.

However, in the present embodiment, the number of summations by the attention amount determination section 60 is not limited to a designated number of times as mentioned above, but instead a non-cumulative electroencephalogram (a single electroencephalogram data) may be used. Even with a non-cumulative electroencephalogram, the attention amount determination section 60 can determine an attention amount. Note that, when an attention amount with respect to a non-cumulative electroencephalogram is determined, it is possible to determine the attention amount with respect to the presented stimulation, and thus it is possible to determine whether the presented stimulation has been perceived (the attention amount was large) or overlooked (the attention amount was small).

At step S606 in FIG. 15, the attention amount determination section 60 performs an arithmetic mean process for the required number of times of electroencephalogram data stored at step S605. Furthermore, from the arithmetic-meaned electroencephalogram data, the attention amount determination section 60 analyzes an amplitude of the event-related potential from 300 milliseconds to 600 milliseconds, and extracts P300. For the attention amount determination, the threshold calculated by the threshold setting section 40 is used, and the amount of attention is determined through a comparison between the arithmetic-meaned P300 amplitude value of the electroencephalogram data and the threshold. Through the comparison, if the P300 amplitude value falls below the threshold (i.e., the P300 amplitude value is smaller than the threshold), the attention amount determination section 60 determines that the driver 10 is in a state of distraction. On the other hand, if the amplitude rises above the threshold (i.e., the P300 amplitude value is equal to the threshold or greater than the threshold), the attention amount determination section 60 determines that the driver 10 is in a state of focused driving. In the example of FIG. 14, the threshold is set to 21.0 μV. The attention amount determination section 60 compares this value and the P300 amplitude.

At step S607 in FIG. 15, the attention amount determination section 60 stores the data of the result determined at step S606 to the storage section 70, for example, or sends it to the display panel 75 for displaying. The stored result can be used later for purposes such as analyzing the driving tendency of the driver 10. Examples of stored information are shown in FIG. 17. The stored information may be, other than the amount of attention as a result of determination, the positions of the presented stimulations, the visual regions of the stimulations (the central visual field or the peripheral visual field), and the points in time of presentation. As the positions of the presented stimulations, relative viewing angles (e.g., the right side of the X axis defining positive, and the upper side of the Y axis defining positive values) are recorded while defining the front center as coordinates (0,0), for example. As the timing of presentation, points in time of presenting visual field stimulations are recorded, and in the case of a peripheral stimulation, whichever one of the focused state or distracted state that corresponds to the result of attention amount determination is recorded.

Hereinafter, a method of utilizing the recorded results of attention amount will be described.

The display panel 75 displays the result for feedback to the driver 10. The same is also true in the case where the attention amount determination section 60 possesses a display means such as a display. Furthermore, in the case where the driving attention amount determination apparatus 1 possesses a communications means, the result may be sent to the exterior of the attention amount determination apparatus 1. For example, assuming that the driving attention amount determination apparatus 1 is connected to a control unit (not shown) of an automobile, when a determination of distractedness is made, control may be performed such that the driving attention amount determination apparatus 1 outputs the result to the control unit of the automobile and that the control unit activates the brakes for automatic braking.

For use in school, the driving attention amount determination apparatus 1 is utilized for the purpose of instructing on safe driving. For example, if the amount of attention lowers and a state of distraction is determined, an alarm sound may be output to notify the driver and the driving instructor of a state of being distracted, by using an audio output means such as a loudspeaker internal to the driving attention amount determination apparatus 1 or an external loudspeaker which is connected to the driving attention amount determination apparatus 1.

In the case where an attention amount determination has been made based on a non-cumulative waveform, it is possible to determine which stimulation has been overlooked; therefore, the positions of overlooked stimulations on the DS display may be indicated with icons, thus providing alarms on overlooked stimulations for the driver in real time. An example of an alarm is shown in FIG. 18A. FIG. 18A is an example where a stimulation is presented in the peripheral visual field, and immediately after the attention amount determination section 60 makes a determination of distractedness, an icon indicating an overlook of the stimulation (an overlook notice icon 141) is displayed at the position of the peripheral stimulation on the DS screen 140. Since the driver is presumably paying attention to the overlook notice icon 141 and not focused on driving while the overlook notice icon 141 is being displayed, central stimulations and peripheral stimulations of the driving attention amount determination apparatus 1 may be prevented from being displayed. Moreover, while the overlook notice icon 141 is being displayed, a process of sending a signal for pausing the video on the DS to the DS may be performed in order to allow the driving instructor in school to provide instructions.

The above description is directed to an example where a feedback is provided in real time when a driver is determined as being distracted. Otherwise, a driving score may be fed back to the driver after finishing driving on the DS. An example of a driving score is shown in FIG. 18B. The driving score is given by using an apparatus which displays a score based on a result of attention amount determination that is stored in the attention amount determination section 60. In FIG. 18B, a driving time, a focused time (a total of time periods determined as focused on driving), and the number of overlooked peripheral stimulations are displayed. According to this score, a driving instructor at school provides instructions. As a method of feedback after driving on a DS, the DS video during the driving may be replayed, and a feedback on the overlooked stimulations may be provided. In that case, a method of displaying an overlook notice icon 141 on the DS video, similarly to FIG. 18A, may be adopted based on the result of attention amount determination stored in the attention amount determination section 60.

Next, a distinction rate in the case where an attention amount determination is made according to the technique of the present invention will be described. The attention determination section 60 compares the P300 amplitude of a response to a peripheral stimulation against the threshold which has been set by the threshold setting section 40 based on responses to central stimulations. Based on the data of an experiment which was actually performed as described above, the inventors have conducted a distinction rate evaluation with respect to 216 trials of peripheral stimulations.

FIG. 19 shows a P300 distribution of responses to peripheral stimulations in the aforementioned experiment. In the graph, the vertical axis represents the P300 potential in units of $\mu V$, and the horizontal axis represents the occurrence probability of each attention amount in units of %. The solid line shows a relationship between P300 amplitude and occurrence probability in the case where the amount of attention is large, whereas the broken line shows a relationship between P300 amplitude and occurrence probability in the case where the amount of attention is small. The P300 distribution of responses to central stimulations in the above experiment is as shown in FIG. 14. A threshold (21.0 $\mu V$) which is set from a median of the P300 distribution of the responses to central stimulations in FIG. 14 is indicated with a dot-dash line in FIG. 19. In such a P300 distribution, the attention amount determination section determines a state of focused driving (large attention amount) when the potential of P300 amplitude is higher than the threshold, or determines a state of distraction (small attention amount) when it falls below the threshold. The inventors have calculated the distinction rate to be a rate at which the attention amount was actually correctly determined. Specifically, the calculation is as follows: distinction rate=a number of instances that were correctly determined/total number of instances.

FIG. 20 shows distinction rate results of performing attention amount determination according to the technique of the present invention. For comparison, FIG. 20 also shows results of performing determination by using optimum thresholds and taking individual differences into consideration as well as results of performing determination by using an average optimum threshold value without considering individual differences.

As compared to a distinction rate of 71.3% according to the technique of the present invention, the distinction rate in the case of individually using optimum thresholds was 73.7%, and the distinction rate in the case of using an average optimum threshold value was 66.1%.

Thus, it can be seen that determination with an accuracy which is close to those associated with optimum thresholds is being made, the accuracy being higher than those associated with a universal threshold.

With the construction and procedure of processing according to the present embodiment, in an apparatus which determines a state of the driver and provides safe driving assistance, a threshold for determination that is adapted to the driver is extracted from an event-related potential of an electroencephalogram signal based on the time point of occurrence of a central stimulation as a starting point. As a result, without previously acquiring electroencephalogram data of driving in a state of focused attention or distraction, an attention amount with respect to a peripheral visual field can be determined. As a result, the attention amount determination can be made as soon as the driver begins driving on a DS, whereby the burden on the driver can be reduced.

In the present embodiment, with respect to an example where the driving attention amount determination apparatus 1 is incorporated in a DS at a driving school, a method of presenting a visual stimulation at an arbitrary position on the DS display has been described. Hereinafter, examples of embodiments in actual-car environments other than the DS environment will be described.

The central stimulation presentation section 30 and the peripheral stimulation presentation section 50 present visual stimulations via projection onto a car windshield.

An exemplary construction of the central stimulation presentation section 30 and the peripheral stimulation presentation section 50 is shown in FIG. 21. FIG. 21 shows stimulations which are projected onto a windshield 161 near the driver's seat. The central stimulation presentation section 30 and the peripheral stimulation presentation section 50 each have a high-luminance projector, and are disposed inside a dashboard 162. For example, assuming that the center of the windshield 161 is the fixation point, the central stimulation presentation section 30 is disposed so as to project a stimulation onto a central visual region 151 spanning 40 degrees from the center, and the peripheral stimulation presentation section 50 is similarly disposed so as to project a stimulation in a peripheral visual region 152 spanning 130 degrees in up and down directions and 180 degrees in right and left directions. The projected stimulations are reflected by the windshield, so as to enter the eyes of the user 10 as visual stimulations.

FIG. 22 shows an example where a projector is not utilized for presenting peripheral stimulations. The peripheral stimulation presentation section 50 is connected to LEDs 164 which are disposed on the ceiling and pillars inside the car, and around sideview mirrors 163. For example, LEDs 164 may be disposed at the respective positions indicated by black circles "●" in FIG. 22. The peripheral stimulation presentation section 50 presents peripheral stimulations by controlling the LEDs 164 to be lit.

Furthermore, an example of a stimulation presenting method utilizing a head-mount display (HMD) will be described. FIG. 23 shows an example where the construction of the present embodiment is incorporated into an HMD 165. The HMD 165 has mounted thereon the construction of the driving attention amount determination apparatus 1 of the present embodiment shown in FIG. 9. As the display panel 75, displays 166 are provided for both eyes. When presenting visual stimulations, the central stimulation presentation section 30 and the peripheral stimulation presentation section 50 send instruction signals to the displays 166 for presenting stimulations, thus causing the stimulations to be displayed on the displays 166 of the HMD. As a result, visual stimulations are presented in the central visual region and the peripheral visual region. In the case where the displays 166 are see-through displays, visual stimulations are presented so as to superposed on the scenery which is actually seen by the driver 10.

Although FIG. 23 illustrates an example where the central stimulation presentation section 30, the threshold setting section 40, the peripheral stimulation presentation section 50, and the attention amount determination section 60 are incorporated in the HMD 165, the aforementioned functional blocks may be provided within the car so as to perform control stimulation presentation and the process of attention amount determination while in communication with the electroencephalogram measurement section 20 and the displays 166. As the communication scheme, generic wireless standards, e.g., Bluetooth or wireless LAN, or some original standard is contemplated.

In the present embodiment, the central visual region and the peripheral visual region are defined based on the center of the direction of travel of the driver's vehicle being regarded as the fixation point, and stimulations are presented. However, in addition to the construction of FIG. 9, a line-of-sight measurement section for detecting the position of the line of sight of the driver 10 may be further provided, and visual regions may be set based on the position of the line of sight and the relative positioning thereof (e.g., viewing angle and distance) for presenting central stimulations and peripheral stimulations.

FIG. 24 shows an example of a line-of-sight measurement section 76. The line-of-sight measurement section 76 measures a fixation point 137 of the driver on a two-dimensional plane 136 which is a projection of a view in the vehicle front in a DS environment, for example. Specifically, in the line-of-sight measurement section 76, a near-infrared light source 131 irradiates the eyeballs with near-infrared as a point light source, and a video of the eyeballs is captured with a CCD camera 132. Then, by using the captured video, the reflection image position detection section 133 detects the position of a corneal reflection image of the light source at the pupil and the corneal surface. A calibration information storing section 135 stores in advance a relationship between corneal reflection image positions and fixation point coordinates in the vehicle front video captured by the imaging section 15. Based on the calibration information, the conversion section 134 measures a line of sight or a fixation point of the driver in the vehicle front video from the position of the corneal reflection image.

Note that the setting of the central visual region, which may fluctuate in accordance with the line of sight, may be done by the central stimulation presentation section 30, while the setting of the peripheral visual region, which is defined in accordance with the central visual region, may be done by the peripheral stimulation presentation section 50.

Embodiment 2

Embodiment 1 has described an example of presenting visual stimulations in the central visual region and the peripheral visual region in an actual-car environment or in a DS environment.

According to the method of presenting visual stimulations of Embodiment 1, when a car is actually being driven, visually-disturbing visual stimulations must be purposely provided on the front, which may be felt annoying to the driver.

Therefore, in the present embodiment, in an actual scene of driving, instead of purposely providing visual stimulations, threshold setting and attention amount determination are to be performed by taking advantage of the visual stimulations which are provided from the external environment. The driving attention amount determination apparatus of the present embodiment has an imaging section for imaging the front of the driver's vehicle, and detects occurrence of any visual stimulation which serves as a starting point for analyzing the event-related potential of an electroencephalogram from the captured video. Then, from the positions at which visual stimulations occurred in the captured video, the central visual region and the peripheral visual region are distinguished, a threshold is set, and an amount of attention is determined.

FIG. 25 shows the block construction of a driving attention amount determination apparatus 2 according to the present embodiment, in which an imaging section 95 is provided. The driving attention amount determination apparatus 2 is based on the driving attention amount determination apparatus 1 (FIG. 9) of Embodiment 1 but the imaging section 95 is added thereto, and the central stimulation presentation section 30 and the peripheral stimulation presentation section 50 of Embodiment 1 are replaced by a stimulation detection section 90. Hereinafter, the respective blocks added to the construction of the driving attention amount determination apparatus 1 (FIG. 9) of Embodiment 1 will be described in detail.

The imaging section 95 is disposed in the front part of the vehicle (e.g., on the dashboard or behind the rear-view mirror) and is aimed outside the car, so that the vehicle front is imaged at 30 frames per second with an angle of view spanning 105 degrees along the vertical direction and 135 degrees along the horizontal direction, for example.

From the video captured by the imaging section 95, the stimulation detection section 90 detects a time point of occurrence of a visual stimulation, which serves as a starting point of analyzing an event-related potential of the electroencephalogram, and at the same time, determines a region in the captured video in which any visual stimulation has occurred. As used herein, a visual stimulation refers to a change in luminance in the video that exceeds a predetermined threshold, e.g., the brake lamps of a preceding vehicle, the winkers of a flanking vehicle, the head lights of an oncoming vehicle, and turning of a traffic light.

The stimulation detection section 90 detects the time point of occurrence of a visual stimulation as defined above, and detects the position of that stimulation. Specifically, it is detected whether the position of the luminance change is in the central visual region or in the peripheral visual region. The method of determination is based on a viewing angle from the center of the captured video (the direction of travel of the driver's vehicle). If the stimulation is contained in the range of a viewing angle of 20 degrees from the center, it is determined as a central stimulation, and if it is outside the central stimulation range but within a region spanning 130 degrees in up and down directions and 180 degrees in right and left directions from the center, it is determined as a peripheral stimulation. Then, if the stimulation is determined as a central stimulation, information indicating the timing of occurrence of this stimulation is sent to the threshold determination section 40, or if it is determined to be in the peripheral visual region, the time point of occurrence of this stimulation is sent to the attention amount determination section 60.

The driving attention amount determination apparatus 2 of the present embodiment significantly differs from the driving attention amount determination apparatus 1 of Embodiment 1 with respect to the stimulation detection section 90. Therefore, by using the flowchart of FIG. 26, the details of the processing by the stimulation detection section 90 will be described below. With respect to the other portions, the description will be omitted because they are similar to those in Embodiment 1.

At step S901, the stimulation detection section 90 receives the video captured by the imaging section 95, and measures a difference in luminance value between adjoining frames of the video. However, in the case where imaging is performed by an onboard camera, the entire video will be moving with the motion of the driver's vehicle, so that merely calculating a difference between adjoining frames will result in a perception that the entire video has changed. Therefore, a corresponding point between the frames (the position of the same object) is calculated, and the difference between the luminance values of the respective corresponding points is calculated. Note that the same object, as referred to herein, may be a rear lamp unit of a preceding vehicle, for example.

At step S902, it is determined from the above difference whether any luminance change that is equal to or greater than a predetermined threshold Th1 has occurred. If such a luminance change has occurred, control proceeds to step S903; if not, control proceeds to step S910. At step S910, the stimulation detection section 90 determines whether the stimulation detection has been ended or not. In other words, it is confirmed whether or not to continue on the stimulation detection.

At step S903, the stimulation detection section 90 records the point in time of luminance change and the position at which the luminance change in the image has occurred, as the visual stimulation. Moreover, the stimulation detection section 90 calculates a viewing angle of the visual stimulation. The viewing angle of a stimulation can be calculated by utilizing the video captured in the direction of travel of the driver's vehicle. More specifically, a viewing angle from the center of the video per unit length, in the image, is prepared in advance. The center of the video corresponds to the fixation point. Then, a distance in the image between the center of the video captured by the stimulation detection section 90 and the coordinates of the stimulation is determined. Next, the determined distance and the viewing angle per unit length are multiplied. As a result, the viewing angle of the stimulation can be determined. A viewing angle as referred to herein is supposed to be the angle between a line of sight connecting an eyeball of the driver 10 and the fixation point and a line segment connecting the eyeball of the driver 10 and the position of the stimulation.

Other methods of viewing angle calculation are also possible. For example, the distance between an eyeball of the driver 10 and the focal position of the captured image (hereinafter referred to as the "image distance") may be set in advance, and the distance in the image between the center of the video captured by the stimulation detection section 90 and the coordinates of the detected stimulation is determined. Next, from a right triangle defined by the determined distance and the image distance, a viewing angle of the stimulation can be calculated. Specifically, it can be calculated as follows: the viewing angle of the stimulation (unit: radian)=ArcTan (the distance between the center of the video and the coordinates of the detected stimulation/image distance).

At step S904, the stimulation detection section 90 determines whether the detected stimulation has occurred in the central visual field or not. Herein, assuming the threshold to be a viewing angle of 20 degrees, it is determined whether or not the viewing angle of the stimulation is equal to or less than 20 degrees. If it is equal to or less than 20 degrees, control proceeds to step S905, where the detected stimulation is detected as a central stimulation.

If a central stimulation is detected, at step S906, the timing of occurrence of the stimulation is sent to the threshold setting section 40, and a process of threshold setting is performed.

If step S904 determines that the detected stimulation is not a central stimulation, the process proceeds to step S907. At step S907, the stimulation detection section 90 determines whether the stimulation has occurred in the peripheral visual field or not. Herein, it is determined whether or not the viewing angle is contained in a range spanning 130 degrees in up and down directions and 180 degrees in right and left directions. If it is contained in this range, control proceeds to step S908, where the detected stimulation is detected as a peripheral stimulation.

If a peripheral stimulation is detected, at step S909, the timing of occurrence of the stimulation is sent to the attention amount determination section 60, and an attention amount determination process with respect to the peripheral stimulation is performed.

On the other hand, if step S907 determines that the detected stimulation is not a peripheral stimulation, either, then the process proceeds to step S910.

At step S910, it is confirmed whether or not to continue on the stimulation detection. If the stimulation detection is to be continued, control returns to step S901, and the stimulation detection is repeated.

In the present embodiment, the determination between the central visual field and the peripheral visual field is based on the angle between the center of the captured video (in the direction of travel of the driver's vehicle) and the coordinates of a detected stimulation. However, in addition to the construction of FIG. 25, a line-of-sight measurement section for detecting the position of the line of sight of the driver 10 may be further provided, and from the viewing angle between the position of the line of sight and the detected stimulation, a determination may be made as to which of the central visual region and the peripheral visual region the visual region falls in. Since the construction of the line-of-sight measurement section is as described in Embodiment 1 by referring to FIG. 24, its description is omitted here. The stimulation detection section 90 may set a central visual region based on the fixation point or the line of sight of the driver as measured by the line-of-sight measurement section, and further set a peripheral visual region which is defined in accordance with the central visual region.

With the above construction and processes, a threshold adapted to each individual can be set while preventing any visual stimulation that may be visually disturbing to the driver from blocking the field of view.

Embodiment 3

The construction of Embodiment 1 has made it possible to set a threshold which is appropriate to each individual for performing an attention amount determination, without measuring an electroencephalogram in a state of focused driving or a state of distraction in advance, or previously acquiring electroencephalogram data of driving in a state of focused attention or distraction.

However, when the attention amount determination apparatus is expected to be incorporated into a private automobile, it is necessary to present a central stimulation every time at the beginning of driving to set a threshold. In this manner, until the threshold setting is finished, it is difficult to determine a state of distraction at the beginning of driving. However, what is preferable is an ability to determine an amount of attention from the beginning of driving.

Therefore, there is a need to set a threshold adapted to each individual so as to allow an attention amount determination to be performed from the beginning of driving. In an environment where the driver is limited, as in a private automobile, it is possible to utilize electroencephalogram data which has been measured in the past.

Now, it can be seen from the graph of FIG. 5 that there is a discrepancy between the average P300 amplitudes in the respective states of large attention amount/small attention amount in the peripheral visual field. FIG. 27 shows a P300 distribution with respect to peripheral stimulations in the above experiment. In the graph of FIG. 27, the vertical axis represents the potential of P300 amplitude (µV), and the horizontal axis represents the occurrence probability (%) at each potential. It can be seen that, just as there is a discrepancy between the P300 amplitude averages in the states of large and small attention amounts in FIG. 5, there are two distribution peaks near 36 µV and 10 µV in the 2300 distribution of FIG. 27. These two distributions can respectively be regarded as distributions of the respective states of large attention amount/small attention amount. Therefore, by calculating a value that distinguishes between these two distributions, it is possible to set a threshold that distinguishes between the states of large attention amount/small attention amount.

In many cases, a private automobile is expected to be used by a specific individual for a long period of time, and each person is expected to conduct driving in both states of being focused on driving and being distracted. Therefore, it is considered that the P300 distribution with respect to peripheral stimulations that has been measured in the past also results in a distribution shape with two peaks as in the distribution of FIG. 27, due to the P300 amplitudes of the two states of being focused on driving and being distracted having been stored.

By taking these into consideration, the inventors have arrived at the attention amount determination apparatus according to the present embodiment. The attention amount determination apparatus of the present embodiment is able to determine the attention amount from the beginning of driving, because of a threshold being set by utilizing a P300 distribution with respect to peripheral stimulations that has been measured in the past.

FIG. 28 shows a block construction of an attention amount determination apparatus 3 of the present embodiment. A functional block that is newly added in the present embodiment is a start threshold setting section 80. The other functional blocks are the same as those in Embodiment 1, and the same numerals as those in FIG. 9 will be used, and the descriptions will be omitted.

The present embodiment assumes that, prior to storing results of determination, the storage section 70 has stored therein the P300 amplitude values with respect to peripheral stimulations that have been extracted by the construction of Embodiment 1.

From the P300 amplitude distribution with respect to peripheral stimulations that is recorded in the storage section 70, the start threshold setting section 80 determines a threshold for attention amount determination.

FIG. 29 is a flowchart of the processing by the attention amount determination apparatus 3 of the present embodiment. In the flowchart of FIG. 29, portions of the processing that are the same as those in Embodiment 1 will be denoted by the same numerals as those in FIG. 9, and the descriptions thereof will be omitted.

Once the attention amount determination apparatus 3 is activated and electroencephalogram recording is begun, the start threshold setting section 80 sets a threshold for attention amount determination at step S80. The start threshold setting section 80 sets a threshold by acquiring previously-measured P300 data with respect to peripheral stimulations that is recorded in the storage section 70 and analyzing the P300 distribution. The details of the processing by the start threshold setting section 80 will be described later.

After the threshold setting, step S4 of enhancing the threshold accuracy or step S5 of determining the amount of attention is executed. When step S5 is executed, a peripheral stimulation is presented at step S50, and after the amount of attention is determined at step S60, the storage section 70 records a P300 amplitude value with respect to the peripheral stimulation at step S70.

Moreover, when a threshold adapted to each individual is set at step S4 of enhancing the threshold accuracy based on a response utilizing a central stimulation, a central stimulation is presented at step S31. The start threshold setting section 80 discards the threshold that was set at step S80, and sets a threshold that is newly ascertained based on the central stimulation at step S41 to perform an attention amount determination. If the re-setting of a threshold utilizing a central stimulation is not performed, an adjustment may be made so that only the process of process S5 of determining an amount of attention is performed at step S26.

Next, the details of the process of setting a start threshold which is performed at step S80 will be described. FIG. 30 is a flowchart showing a flow of processes of step S80 that are performed by the start threshold setting section 80. The setting of a start threshold is performed by utilizing peripheral stimulation-P300 amplitudes that have been recorded in the storage section 70 in the past.

At step S801, P300 amplitude values with respect to peripheral stimulations are received from the storage section 70. FIG. 31 shows an exemplary format of the received data. In the example of FIG. 31, as the recorded information of P300 amplitudes, pieces of information each indicating a point in time at which a stimulation is presented and a P300 amplitude value in response thereto are recorded in chronological order.

At step S802 in FIG. 30, the start threshold setting section 80 performs an analysis of the P300 distribution. With respect to the entirety of the received P300 data, the start threshold setting section 80 examines P300 amplitude values and occurrence frequencies thereof, thus analyzing the P300 distribution with respect to peripheral stimulations. FIG. 27 shows an exemplary result of analyzing 216 peripheral stimulation-P300's. This distribution analysis may be performed for all of the data that is recorded in the storage section 70, or the analysis may be made by only utilizing the responses to peripheral stimulations during the most recent driving. In the latter case, based on the time information of the received data, the analysis may be performed with respect to the P300 amplitude data in a certain time period. By performing an analysis limited to the most recent data, it is possible to set a threshold which follows the changes in P300 response within each individual.

At step S803 and step S804 in FIG. 30, distribution peaks of large and small amounts of attention are extracted in the analyzed P300 distribution data. If a sufficient data amount has been stored, two distribution peaks should exist because of the tendency that there is a discrepancy between P300 amplitude averages in the states of large and small attention amounts. Since the two distribution peaks appear in the form of local maximums, detection of distribution peaks is performed by extracting two local maximums with large occurrence probabilities.

At step S803, from the P300 distribution graph, local maximums of occurrence probability are detected. FIG. 32A shows examples of extracted local maximums. The positions of arrows in FIG. 32A are the positions of detected local maximums.

At step S804, from among the plurality of local maximums, two local maximums whose occurrence probabilities are the largest are extracted. These two extracted local maximums are considered as the distribution peaks of large and small amounts of attention. FIG. 32B shows an example of extracted distribution peaks. In the example of FIG. 32B, 12.5 µV and 37.5 µV are calculated as the local maximums.

In the above example, the distribution peaks of large and small amounts of attention are extracted by detecting local maximums with highest occurrence probabilities. However, this technique is exemplary, and is not a limitation.

At step S805 in FIG. 30, a threshold for distinguishing between distributions of large and small amounts of attention is calculated. The calculation of the threshold is performed by calculating a median of the distribution peaks of large and small amounts of attention. By utilizing a median, the two distributions can be impartially separated without being affected by an imbalance in P300 amplitude value between the distribution peaks. In the example of FIG. 32B, 21.0 µV is calculated as a median of the occurrence frequency distribution from 12.5 µV to 37.5 µV.

At step S806, by using the calculated median is set as a threshold in the attention amount determination section 60. In the example of FIG. 32B, 21.0 µV is set as a start threshold for attention amount determination.

A result of performing a determination by utilizing a recorded peripheral stimulation-P300 distribution through the above process is shown in FIG. 33. Although the average distinction rate of 68.7% is inferior to that in Embodiment 1, the accuracy is improved almost by 3% as compared to that in the case of utilizing a threshold which does not take individual differences into consideration, i.e., 66.1%.

With the construction and procedure of processing according to the present embodiment, in an apparatus which determines a state of the driver and provides safe driving assistance, there is no need to wait until a sufficient amount of P300 data for stimulations in the central visual field is stored for setting a threshold, thus making it possible to immediately make an attention amount determination from the beginning of driving.

Although the description of the above embodiment illustrates a process of setting a start threshold based on the peripheral stimulation-P300 distribution stored in the storage section 70, the method of setting a threshold is not limited thereto. For example, a threshold for attention amount determination which was utilized in the previous time may be utilized as it is.

Moreover, P300 data of central stimulations may also be stored in the storage section 70, and setting of a start threshold may be performed by utilizing a median of the central stimulation-P300 distribution. With the above method of setting a start threshold, a start threshold can be set even when the data amount of peripheral stimulation-P300 is not sufficient.

The above embodiments are described based on the assumption that a single specific driver employs attention amount determination. In the case where a plurality of users exist for the attention amount determination apparatus, a user determination means may be further provided to distinguish between users and switch between store data for use in the threshold setting. As the user determination means, techniques of making a distinction based on the seat position among seats, the mirror position, and differences between the car keys used.

The above embodiments are described by illustrating the electroencephalogram measurement section (FIG. 9, FIG. 25, FIG. 28), the imaging section, and the stimulation detection section (FIG. 25) as constituent elements of the driving attention amount determination apparatus. However, these may not be essential constituent elements of the driving attention amount determination apparatus. The electroencephalogram measurement section and/or the imaging section may be external devices separate from the driving attention amount determination apparatus. In that case, the driving attention amount determination apparatus may receive from such devices the electroencephalogram data and video data acquired through imaging, and perform the same processes as the above-described processes. Moreover, it may receive data of stimulations contained in the video of the vehicle front, data of the time points of occurrence of stimulations, and data of results of detection as to whether the positions in the video at which stimulations occurred are within the central visual region or the peripheral visual region of the driver, and perform the same processes as the above-described processes.

In the case where the aforementioned electroencephalogram measurement section, the imaging section, and/or the stimulation detection section are not constituent elements of the driving attention amount determination apparatus, but instead supply data to the driving attention amount determination apparatus, the driving attention amount determination apparatus may be implemented as a computer executing a computer program.

Such a computer program contains instructions for executing procedures described by the flowcharts illustrated in the present application. By executing such a computer program, a computer functions as the respective constituent elements of the aforementioned driving attention amount determination apparatus. Such a computer program may be distributed on the market in the form of a product recorded on a storage medium, such as a CD-ROM, or transmitted via telecommunication lines such as the Internet. Note that the state-of-attention determination apparatuses according to the above embodiments and variants can also be implemented in hardware, e.g., a DSP composed of a computer program incorporated in a semiconductor circuit.

The storage section 70 and the display panel 75 also may not be essential constituent elements of the driving attention amount determination apparatus. The storage section 70 and the display panel 75 may be an external hard disk drive and a display device connected to the driving attention amount determination apparatus, for example.

The driving attention amount determination apparatus according to the present invention is useful for accident prevention concerning events that may occur in the peripheral visual region of a driver, e.g., a sudden intrusion of a vehicle or a rushing out of a pedestrian. It is also effective for a driving evaluation apparatus utilizing a driving simulator at a driving school or the like. Furthermore, in the case where it is constructed as a head-mount display type apparatus, it has applications as apparatuses for providing safe assistance while riding a bicycle or walking, or for determining allocation of attention to surrounding customers or situations as in a service trade, or the like.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed:

1. A driving attention amount determination apparatus comprising:
    an imaging section for imaging a vehicle front;
    a stimulation detection section for detecting a stimulation contained in a video captured by the imaging section and a time point of occurrence of the stimulation, and detecting whether a position of occurrence of the stimulation in the video is in a central visual region or a peripheral visual region of a driver;
    an electroencephalogram measurement section for measuring an electroencephalogram signal of the driver;
    a threshold setting section for setting a determination threshold for attention amount determination from a distribution of amplitude of an event-related potential in the electroencephalogram signal based on a point of presenting a stimulation in the central visual region as a starting point; and
    an attention amount determination section for determining an amount of attention through a comparison between the determination threshold and an amplitude of an event-related potential in the electroencephalogram signal based on a point of presenting a stimulation in the peripheral visual region as a starting point.

2. The driving attention amount determination apparatus of claim 1, further comprising a line-of-sight measurement section for measuring a line of sight of the driver, wherein
    the stimulation detection section detects whether the stimulation is contained in the central visual region or the peripheral visual region of the driver in accordance with the line of sight of the driver as detected by the line-of-sight measurement section at the time point of occurrence of the stimulation.

3. The driving attention amount determination apparatus of claim 1, further comprising:
    a storage section for storing P300 amplitudes of an event-related potential of the driver generated by the driver in the past in response to stimulations presented by the peripheral stimulation presentation section; and
    a start threshold setting section for extracting two peaks contained in the stored distribution of P300 amplitudes, and setting the determination threshold by utilizing the two peaks.

4. The driving attention amount determination apparatus of claim 3, wherein the start threshold setting section sets a median of the two peaks as the determination threshold.

5. A method of driving attention amount determination, comprising:
    an electroencephalogram measurement step of measuring an electroencephalogram signal of a driver;
    a central stimulation presenting step of presenting a visual stimulation in a central visual field of the driver;
    a peripheral stimulation presenting step of presenting a visual stimulation in a peripheral visual field of the driver;
    a threshold setting step of setting a determination threshold for attention amount determination from a distribution of amplitude of an event-related potential in the electroencephalogram signal based on a point of presenting the stimulation in the central visual field as a starting point; and
    an attention amount determining step of determining an amount of attention through a comparison between the determination threshold and an amplitude of an event-related potential in the electroencephalogram signal based on a point of presenting the stimulation in the peripheral visual field as a starting point.

6. The method of driving attention amount determination of claim 5, wherein,
    the amplitude of an event-related potential based on the point of presenting the stimulation in the central visual field as a starting point is an amplitude of a P300 which is a positive component in a zone from 300 milliseconds to 600 milliseconds based on a point of presenting a visual stimulation in the central visual field as a starting point; and
    the amplitude of an event-related potential based on the point of presenting the stimulation in the peripheral visual field as a starting point is an amplitude of a P300 which is a positive component in a zone from 300 milliseconds to 600 milliseconds based on a point of presenting a visual stimulation in the peripheral visual field as a starting point.

7. The method of driving attention amount determination of claim 5, wherein,
the attention amount determining step compares the determination threshold and the amplitude value of an event-related potential based on the point of presenting the stimulation in the peripheral visual field as a starting point, and
if the amplitude value is equal to or greater than the determination threshold, determines that the amount of attention is high, and
if the amplitude value is smaller than the determination threshold, determines that the amount of attention is low.

8. A non-transitory computer-readable medium storing a computer program to be executed by a computer, for determining an amount of attention,
the computer program causing the computer to execute:
a step of receiving a measured electroencephalogram signal of a driver;
a central stimulation presenting step of presenting a visual stimulation in a central visual field of the driver;
a peripheral stimulation presenting step of presenting a visual stimulation in a peripheral visual field of the driver;
a threshold setting step of setting a determination threshold for attention amount determination from a distribution of amplitude of an event-related potential in the electroencephalogram signal based on a point of presenting the stimulation in the central visual field as a starting point; and
an attention amount determining step of determining an amount of attention through a comparison between the determination threshold and an amplitude of an event-related potential in the electroencephalogram signal based on a point of presenting the stimulation in the peripheral visual field as a starting point.

9. A driving attention amount determination apparatus for receiving data of a stimulation contained in a video of a vehicle front captured by an imaging section, data of a time point of occurrence of the stimulation, and data of a result of detection as to whether a position of occurrence of the stimulation in the video is in a central visual region or a peripheral visual region of a driver, the driving attention amount determination apparatus comprising:
a threshold setting section for setting a determination threshold for attention amount determination from a distribution of amplitude of an event-related potential in an electroencephalogram signal based on a point of presenting a stimulation in the central visual region as a starting point, the electroencephalogram signal being measured by an electroencephalogram measurement section for measuring an electroencephalogram signal; and
an attention amount determination section for determining an amount of attention through a comparison between the determination threshold and an amplitude of an event-related potential in the electroencephalogram signal based on a point of presenting a stimulation in the peripheral visual region as a starting point.

* * * * *

UNITED STATES PATENT AND TRADEMARK OFFICE
CERTIFICATE OF CORRECTION

Page 1 of 1

PATENT NO. : 9,117,124 B2
APPLICATION NO. : 14/247550
DATED : August 25, 2015
INVENTOR(S) : Yoshihisa Terada and Koji Morikawa It is certified that error appears in the above-identified patent and that said Letters Patent is hereby corrected as shown below:

Title Page, Insert Item (30), which should read:

-- (30)   Foreign Application Priority Data

October 15, 2009 (JP)....................... 2009-238057 --.

Signed and Sealed this
Eighth Day of March, 2016

Michelle K. Lee
*Director of the United States Patent and Trademark Office*